United States Patent
Slocum et al.

(10) Patent No.: US 11,925,359 B2
(45) Date of Patent: Mar. 12, 2024

(54) ROTARY ELECTRIC SURGICAL HAMMER IMPACT TOOL

(71) Applicant: Zimmer, Inc., Warsaw, IN (US)

(72) Inventors: Alexander Slocum, Bow, NH (US); Nitin Goyal, Mclean, VA (US)

(73) Assignee: Zimmer, Inc., Warsaw, IN (US)

( * ) Notice: Subject to any disclaimer, the term of this patent is extended or adjusted under 35 U.S.C. 154(b) by 45 days.

(21) Appl. No.: 17/587,794

(22) Filed: Jan. 28, 2022

(65) Prior Publication Data

US 2022/0240946 A1 Aug. 4, 2022

Related U.S. Application Data

(60) Provisional application No. 63/143,514, filed on Jan. 29, 2021.

(51) Int. Cl.
*A61B 17/16* (2006.01)
*A61B 17/00* (2006.01)
*A61B 90/50* (2016.01)

(52) U.S. Cl.
CPC ...... *A61B 17/1604* (2013.01); *A61B 17/1628* (2013.01); *A61B 90/50* (2016.02);
(Continued)

(58) Field of Classification Search
CPC . A61B 17/1604; A61B 90/50; A61B 17/1628; A61B 2017/00017; A61B 2560/0204
See application file for complete search history.

(56) References Cited

U.S. PATENT DOCUMENTS

| 974,267 A | 11/1910 | Hennessy |
| 2,542,695 A | 2/1951 | Neff et al. |

(Continued)

FOREIGN PATENT DOCUMENTS

| CH | 701397 A2 | 1/2011 |
| CN | 2423872 Y | 3/2001 |

(Continued)

OTHER PUBLICATIONS

"International Application Serial No. PCT/US2021/058776, International Preliminary Report on Patentability dated May 25, 2023", 10 pgs.

(Continued)

*Primary Examiner* — Kevin T Truong
*Assistant Examiner* — Diana Jones
(74) *Attorney, Agent, or Firm* — SCHWEGMAN LUNDBERG & WOESSNER, P.A.

(57) ABSTRACT

Disclosed herein are rotary electric surgical hammer impact tools and methods of use thereof. The rotary electric surgical hammer impact tools can include a too body, a motor located within the tool body, a shaft operatively couple to the motor, a disk hammer element, and a tool holder element. The disk hammer element can be connected to the shaft and include a radial impact projection. The tool holder element can include a shaft configured to support an implement at one end and a C-shaped structure straddling the disk hammer element. Axial movement within the tool body can cause the radial impact projection to impart impacts to the tool holder element.

20 Claims, 17 Drawing Sheets

(52) U.S. Cl.
CPC ............... *A61B 2017/00017* (2013.01); *A61B 2560/0204* (2013.01)

(56) References Cited

U.S. PATENT DOCUMENTS

| | | | |
|---|---|---|---|
| 3,450,215 A | 6/1969 | Emery | |
| 3,472,323 A | 10/1969 | Hall | |
| 3,626,935 A | 12/1971 | Pollock et al. | |
| 3,752,161 A | 8/1973 | Bent | |
| 4,298,074 A | 11/1981 | Mattchen | |
| 4,466,429 A * | 8/1984 | Loscher | A61B 17/1659 |
| | | | 606/85 |
| 4,651,833 A | 3/1987 | Karpf et al. | |
| 4,834,092 A | 5/1989 | Alexson et al. | |
| 5,057,112 A | 10/1991 | Sherman et al. | |
| 5,108,400 A | 4/1992 | Appel et al. | |
| 5,152,352 A | 10/1992 | Mandanis | |
| 5,163,519 A | 11/1992 | Mead et al. | |
| 5,210,918 A | 5/1993 | Wozniak | |
| 5,282,805 A | 2/1994 | Richelsoph et al. | |
| 5,352,230 A | 10/1994 | Hood | |
| 5,353,230 A | 10/1994 | Maejima et al. | |
| 5,431,660 A | 7/1995 | Burke | |
| 5,485,887 A | 1/1996 | Mandanis | |
| 5,553,675 A | 9/1996 | Pitzen et al. | |
| 6,126,694 A | 10/2000 | Gray, Jr. | |
| 6,159,214 A | 12/2000 | Michelson | |
| 6,264,660 B1 | 7/2001 | Schmidt et al. | |
| 6,264,661 B1 | 7/2001 | Jerger et al. | |
| 6,368,324 B1 | 4/2002 | Dinger | |
| 6,520,266 B2 | 2/2003 | Bongers-Ambrosius et al. | |
| 6,626,913 B1 | 9/2003 | Mckinnon et al. | |
| 6,814,738 B2 | 11/2004 | Naughton et al. | |
| 7,090,677 B2 | 8/2006 | Fallin et al. | |
| 7,189,241 B2 | 3/2007 | Yoon et al. | |
| 7,637,327 B2 | 12/2009 | Grünig | |
| 8,002,776 B2 | 8/2011 | Liu et al. | |
| 8,444,647 B2 | 5/2013 | Walen et al. | |
| 8,465,492 B2 | 6/2013 | Estes | |
| 8,556,901 B2 | 10/2013 | Anthony et al. | |
| 8,602,124 B2 | 12/2013 | Pedicini | |
| 8,695,726 B2 * | 4/2014 | Pedicini | A61B 17/1628 |
| | | | 173/132 |
| 8,894,654 B2 | 11/2014 | Anderson | |
| 8,936,105 B2 | 1/2015 | Pedicini | |
| 8,936,106 B2 | 1/2015 | Pedicini | |
| 9,168,154 B2 | 10/2015 | Behzadi | |
| 9,186,158 B2 | 11/2015 | Anthony et al. | |
| 9,198,675 B2 | 12/2015 | Nelson et al. | |
| 9,220,612 B2 | 12/2015 | Behzadi | |
| 9,554,965 B2 | 1/2017 | Foehrenbach | |
| 9,629,641 B2 | 4/2017 | Ferro et al. | |
| 9,649,202 B2 | 5/2017 | Behzadi | |
| 9,877,734 B2 | 1/2018 | Anderson | |
| 9,901,354 B2 | 2/2018 | Pedicini | |
| 9,931,151 B2 | 4/2018 | Donald et al. | |
| 9,943,318 B2 | 4/2018 | Anthony et al. | |
| RE46,954 E | 7/2018 | Pedicini | |
| 10,028,754 B2 * | 7/2018 | Johnson | A61B 17/1659 |
| RE46,979 E | 8/2018 | Pedicini | |
| 10,159,500 B2 | 12/2018 | Chavarria et al. | |
| 10,172,722 B2 | 1/2019 | Behzadi | |
| 10,245,160 B2 | 4/2019 | Behzadi | |
| 10,245,162 B2 | 4/2019 | Behzadi | |
| 10,251,663 B2 | 4/2019 | Behzadi | |
| 10,299,930 B2 | 5/2019 | Behzadi | |
| 10,342,591 B2 | 7/2019 | Pedicini | |
| 10,368,882 B2 | 8/2019 | Ferro et al. | |
| 10,413,425 B2 | 9/2019 | Behzadi | |
| 10,426,540 B2 | 10/2019 | Behzadi | |
| 10,441,244 B2 | 10/2019 | Behzadi | |
| 10,456,271 B2 | 10/2019 | Behzadi | |
| 10,463,505 B2 | 11/2019 | Behzadi | |
| 10,470,897 B2 | 11/2019 | Behzadi | |
| 10,478,318 B2 | 11/2019 | Behzadi | |
| 10,603,173 B2 | 3/2020 | Carr et al. | |
| RE47,963 E | 4/2020 | Pedicini | |
| 10,610,379 B2 | 4/2020 | Behzadi | |
| RE47,997 E | 5/2020 | Pedicini | |
| 10,653,533 B2 | 5/2020 | Behzadi | |
| 10,660,767 B2 | 5/2020 | Behzadi | |
| 10,729,559 B2 | 8/2020 | Behzadi et al. | |
| RE48,184 E | 9/2020 | Pedicini | |
| RE48,251 E | 10/2020 | Pedicini | |
| 2011/0270256 A1 | 11/2011 | Nelson et al. | |
| 2012/0172939 A1 | 7/2012 | Pedicini | |
| 2012/0215267 A1 | 8/2012 | Pedicini | |
| 2012/0259339 A1 | 10/2012 | Hood et al. | |
| 2013/0261681 A1 | 10/2013 | Bittenson | |
| 2018/0055518 A1 | 3/2018 | Pedicini | |
| 2018/0055552 A1 | 3/2018 | Pedicini | |
| 2018/0318089 A1 | 11/2018 | Carr et al. | |
| 2018/0360464 A1 | 12/2018 | Irvine | |
| 2019/0167434 A1 | 6/2019 | Satterthwaite et al. | |
| 2019/0183554 A1 | 6/2019 | Pedicini | |
| 2019/0247057 A1 | 8/2019 | Anderson | |
| 2019/0282286 A1 | 9/2019 | Pedicini | |
| 2022/0142693 A1 | 5/2022 | Slocum et al. | |
| 2022/0226033 A1 | 7/2022 | Slocum et al. | |
| 2022/0240947 A1 | 8/2022 | Marinkovich | |
| 2022/0240998 A1 | 8/2022 | Slocum | |
| 2022/0273317 A1 | 9/2022 | Levy | |
| 2023/0240735 A1 | 8/2023 | Doyle | |

FOREIGN PATENT DOCUMENTS

| | | |
|---|---|---|
| CN | 204863450 U | 12/2015 |
| CN | 116801840 A | 9/2023 |
| DE | 102010017726 A1 | 1/2011 |
| EP | 0290375 A1 | 11/1988 |
| FR | 2054809 A5 | 5/1971 |
| WO | WO-8802246 A2 | 4/1988 |
| WO | WO-8906516 A1 | 7/1989 |
| WO | WO-2008130904 A2 | 10/2008 |
| WO | 2016112397 | 7/2016 |
| WO | WO-2018044348 A1 | 3/2018 |
| WO | WO-2018217250 A1 | 11/2018 |
| WO | WO-2022103835 A1 | 5/2022 |
| WO | WO-2022159704 A1 | 7/2022 |
| WO | WO-2022165215 A1 | 8/2022 |
| WO | WO-2022165223 A1 | 8/2022 |
| WO | WO-2022165357 A1 | 8/2022 |
| WO | WO-2022182772 A1 | 9/2022 |

OTHER PUBLICATIONS

"International Application Serial No. PCT/US2022/013312, International Preliminary Report on Patentability dated Aug. 3, 2023", 12 pgs.

"International Application Serial No. PCT/US2022/014368, International Preliminary Report on Patentability dated Aug. 10, 2023", 10 pgs.

"International Application Serial No. PCT/US2022/014380, International Preliminary Report on Patentability dated Aug. 10, 2023", 9 pgs.

"International Application Serial No. PCT/US2022/014596, International Preliminary Report on Patentability dated Aug. 10, 2023", 7 pgs.

"International Application Serial No. PCT/US2021/058776, International Search Report dated Feb. 9, 2022", 5 pgs.

"International Application Serial No. PCT/US2021/058776, Written Opinion dated Feb. 9, 2022", 8 pgs.

"International Application Serial No. PCT/US2022/013312, International Search Report dated Jun. 24, 2022", 6 pgs.

"International Application Serial No. PCT/US2022/013312, Invitation to Pay Additional Fees dated May 3, 2022", 5 pgs.

"International Application Serial No. PCT/US2022/013312, Written Opinion dated Jun. 24, 2022", 10 pgs.

"International Application Serial No. PCT/US2022/014368, International Search Report dated May 30, 2022", 7 pgs.

(56) References Cited

OTHER PUBLICATIONS

"International Application Serial No. PCT/US2022/014368, Written Opinion dated May 30, 2022", 8 pgs.
"International Application Serial No. PCT/US2022/014380, International Search Report dated Jun. 24, 2022", 6 pgs.
"International Application Serial No. PCT/US2022/014380, Invitation to Pay Additional Fees dated May 3, 2022", 5 pgs.
"International Application Serial No. PCT/US2022/014380, Written Opinion dated Jun. 24, 2022", 7 pgs.
"International Application Serial No. PCT/US2022/014596, International Search Report dated May 10, 2022", 4 pgs.
"International Application Serial No. PCT/US2022/014596, Written Opinion dated May 10, 2022", 5 pgs.
"International Application Serial No. PCT/US2022/017537, International Search Report dated Jun. 1, 2022", 4 pgs.
"International Application Serial No. PCT/US2022/017537, Written Opinion dated Jun. 1, 2022", 5 pgs.
Budimir, Miles, "What is a rack and roller pinion?", [Online]. Retrieved from the Internet: <https://www.motioncontroltips.com/rack-roller-pinion/>, (Nov. 10, 2017), 13 pgs.
Nexen, "Rack and Roller Pinion System", [Online]. Retrieved from the Internet: <https://www.nexengroup.com/nxn/products/prod-nav/Ip/Roller+Pinion+System>, (Accessed online Apr. 27, 2021), 10 pgs.
"International Application Serial No. PCT/US2022/017537, International Preliminary Report on datedmailed Sep. 7, 2023", 7 pgs.
"International Application Serial No. PCT US2022 014368, Invitation to Pay Additional Fees dated Apr. 5, 2022", 10 pages.

* cited by examiner

ROTARY ELECTRIC SURGICAL HAMMER IMPACT TOOL

PRIORITY CLAIM

The present application claims priority to U.S. Provisional Application No. 63/143,514, entitled "Rotary Electric Hammer Impact Tool," filed on Jan. 29, 2021; the contents of which are hereby incorporated by reference in their entirety.

FIELD OF THE DISCLOSURE

The present disclosure relates generally to surgical instruments and use thereof. More specifically, the present disclosure relates to a rotary surgical impact tool and methods of use thereof.

BACKGROUND

Orthopedic surgeons commonly utilize tools for cutting or carving bone that require a hammer or mallet to transmit an impaction force to the tool. An example is a broach tool used to prepare the proximal end of a femur to receive the stem of a hip implant. Such broaches can be used with a hammer wielded by the physician or with a pneumatic "jackhammer" like tool. However, striking a broach tool with a hammer can be tiresome and can cause high stresses on the physician's own joints, such as the shoulder joint. Furthermore, pneumatic impact tools require connection to an air hose, which can be inconvenient and can potentially limit the physician's ability to orient the tool in the desired manner.

SUMMARY

The following, non-limiting examples, detail certain aspects of the present subject matter to solve the challenges and provide the benefits discussed herein, among others.

Example 1 is a rotary electric surgical hammer impact tool comprising: a tool body, a motor located within the tool body; a shaft operatively coupled to the motor; a disk hammer element connected to the shaft, the disk hammer element including a radial impact projection; and a tool holder element comprising a shaft configured to support an implement at one end, the shaft of the tool holder element comprising a C-shaped structure straddling the disk hammer element and including opposing forward and rearward impact faces that are spaced, wherein the tool holder element is configured to move axially within the tool body when the implement is pressed against a work surface to bring the forward impact face into alignment to be engaged by the radial impact projection to impart forward impacts to the tool holder element, and wherein the tool holder element is configured to move axially within the tool body when the tool is pulled away from the work surface to bring the rearward impact face into alignment to be engaged by the radial impact projection to impart rearward impacts to the tool holder element.

In Example 2, the subject matter of Example 1 optionally includes wherein a rotational direction of the shaft connected to the motor is changed from a first direction for delivering forward impacts to a second direction for delivering rearward impacts.

In Example 3, the subject matter of any one or more of Examples 1-2 optionally include bearings supporting the shaft of the tool holder element.

In Example 4, the subject matter of any one or more of Examples 1-3 optionally include wherein the motor is configured to rotate the disk hammer element over a partial revolution to deliver the impacts.

In Example 5, the subject matter of any one or more of Examples 1-4 optionally include wherein the radial impact projection of the disk hammer element has a metallic impact surface.

In Example 6, the subject matter of any one or more of Examples 1-5 optionally include wherein the radial impact projection of the disk hammer element has a polymer material impact surface.

In Example 7, the subject matter of any one or more of Examples 1-6 optionally include a sensor arranged to detect impacts on the toll holder element, and a controller configured to reverse rotation of motor to reverse rotation of the disk hammer element.

In Example 8, the subject matter of any one or more of Examples 1-7 optionally include a control electronics and a battery in electrical communication with the control electronics, the control electronics and the battery disposed within the tool body.

In Example 9, the subject matter of any one or more of Examples 1-8 optionally include wherein the shaft of the tool holder element is arranged generally perpendicular to a rotational axis of the motor.

In Example 10, the subject matter of any one or more of Examples 1-9 optionally include a handle extending perpendicular to the tool body.

In Example 11, the subject matter of any one or more of Examples 1-10 optionally include a microphone disposed in the tool body and in electrical communication with a controller, the controller configured to activate the motor based upon voice commands.

In Example 12, the subject matter of any one or more of Examples 1-11 optionally include wherein the disk hammer element includes a plurality of swinging hammer elements mounted thereon.

In Example 13, the subject matter of any one or more of Examples 1-12 optionally include a controller operative to perform operations comprising: determining an estimate of a bone quality; and increasing or decreasing an impact force generated by the linear electric surgical hammer impact tool based on the estimate of the bone quality.

In Example 14, the subject matter of any one or more of Examples 1-13 optionally include a controller operative to perform operations comprising: determining a displacement of a tool attached to the tool holder; and increasing or decreasing an impact force generated by the linear electric surgical hammer impact tool based on the displacement of the tool.

Example 15 is a rotary electric surgical hammer impact tool comprising: an impact wrench having an impacting mechanism configured to deliver rotary impacts to an output shaft; an elongated tool arm mounted to the output shaft and extending perpendicular to an axis of the output shaft; and a tool implement mounted to an end of the elongated tool arm, the tool implement extending generally perpendicular to the end of the elongated tool arm.

In Example 16, the subject matter of Example 15 optionally includes wherein the tool implement is connected to the elongated tool arm by a pin.

Example 17 is a method of controlling a rotary electric surgical hammer impact tool for preparing a bone for receiving a prosthetic device, the method comprising: setting an initial impact force level of the rotary electric surgical hammer impact tool based upon an estimated bone quality; operating the rotary electric surgical hammer impact tool at the set initial impact level; monitoring an amount of a tool advancement into the bone; and increase or decreasing the impact level force by a predetermined amount based upon a detected amount of advancement of the tool into the bone.

In Example 18, the subject matter of Example 17 optionally includes monitoring an amount of a tool advancement into the bone and decreasing the impact level force by a predetermined amount based upon a detected amount of advancement of the tool into the bone.

In Example 19, the subject matter of any one or more of Examples 17-18 optionally include wherein the bone quality is based upon a bone quality score including at least three bone quality levels.

In Example 20, the subject matter of any one or more of Examples 17-19 optionally include wherein the bone quality score is determined by detecting a position change of a broaching tool within a bone during an initial operation of the impact tool, wherein a maximum movement of the broaching tool indicates low bone quality, a mid-level of movement of the broaching tool means a medium bone quality and a minimal amount of movement of the broaching tool within the bone means a high bone quality.

In Example 21, the surgical impact tools, systems, and/or methods of any one or any combination of Examples 1-20 can optionally be configured such that all elements or options recited are available to use or select from.

BRIEF DESCRIPTION OF THE FIGURES

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

As an alternative to a pneumatic piston driven system, disclosed herein are electrically driven systems. Specifically, the rotary electric surgical hammer impact tools disclosed herein can include a tool body, a shaft driven by a motor, a hammer element, and a tool holder used to generate impact forces.

As disclosed herein, a rotary electric surgical hammer impact tool can include a tool body, a shaft, a disk element, and a tool holder element. A motor can be disposed within the tool body. The shaft can be driven by the motor. The disk element, sometimes called a disk hammer element, can be connected to the shaft and can include a radial impact projection. The tool holder element can include a shaft supporting an implement at one end. The shaft can further include a structure, such as a C-shaped structure, straddling the disk hammer element. The structure can include opposing forward and rearward impact faces that are spaced such that as an implement, such as a broach, is pressed against a work surface (e.g., bone), the tool holder element can move axially within the tool body to bring the forward impact face into alignment to be engaged by the radial impact projection to impart forward impacts to the tool holder element. As the rotary electric surgical hammer impact tool is pulled away from the work surface, the tool holder element can move axially within the tool body to bring the rearward impact face into alignment to be engaged by the radial impact projection to impart rearward impacts to the tool holder element.

The above discussion is intended to provide an overview of subject matter of the present patent application. It is not intended to provide an exclusive or exhaustive explanation of the invention. The description below is included to provide further information about the present patent application.

Figure 1:
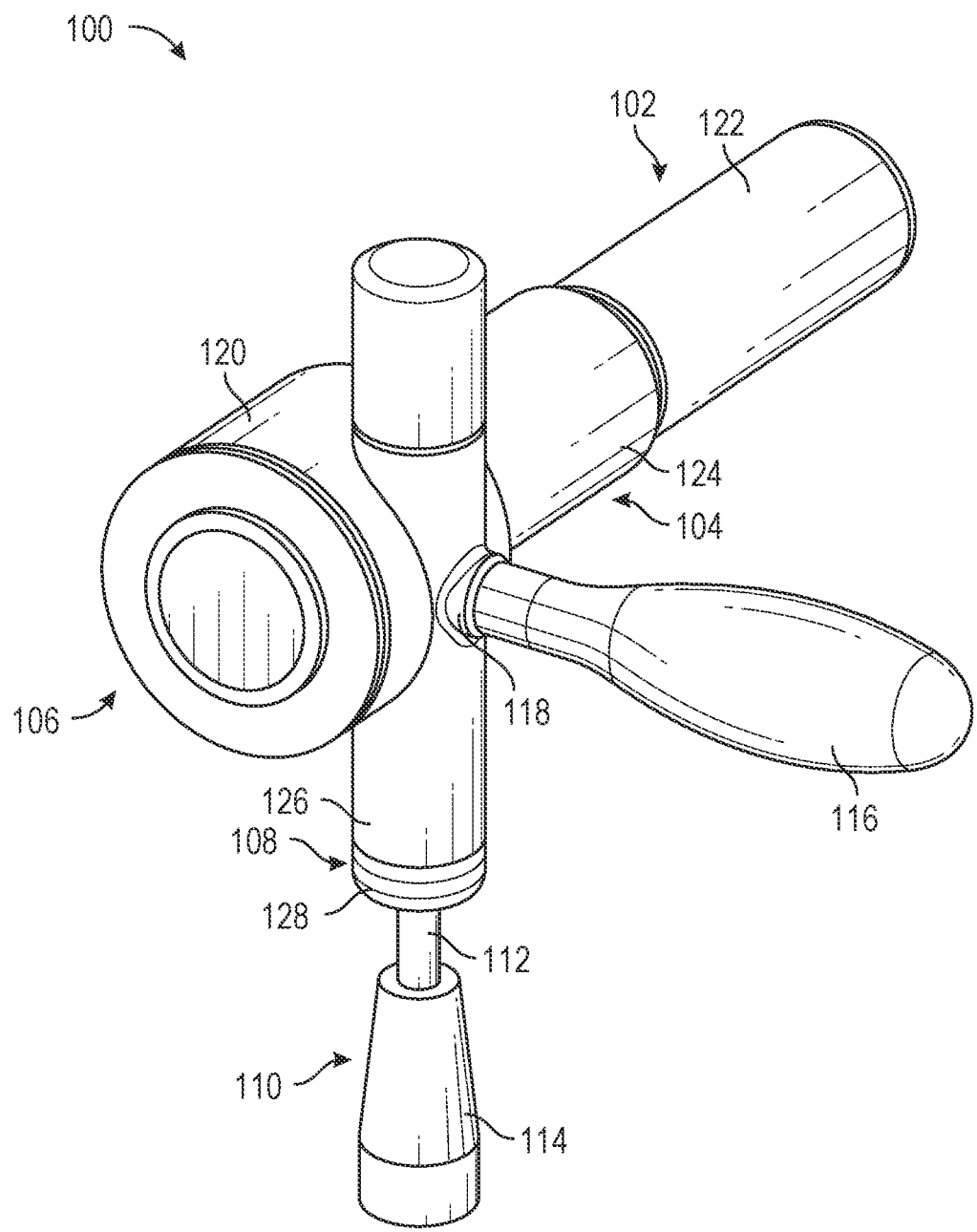
FIG. 1 shows an isometric view of a rotary electric surgical hammer impact tool in accordance with at least one example of this disclosure.
Figure 2:
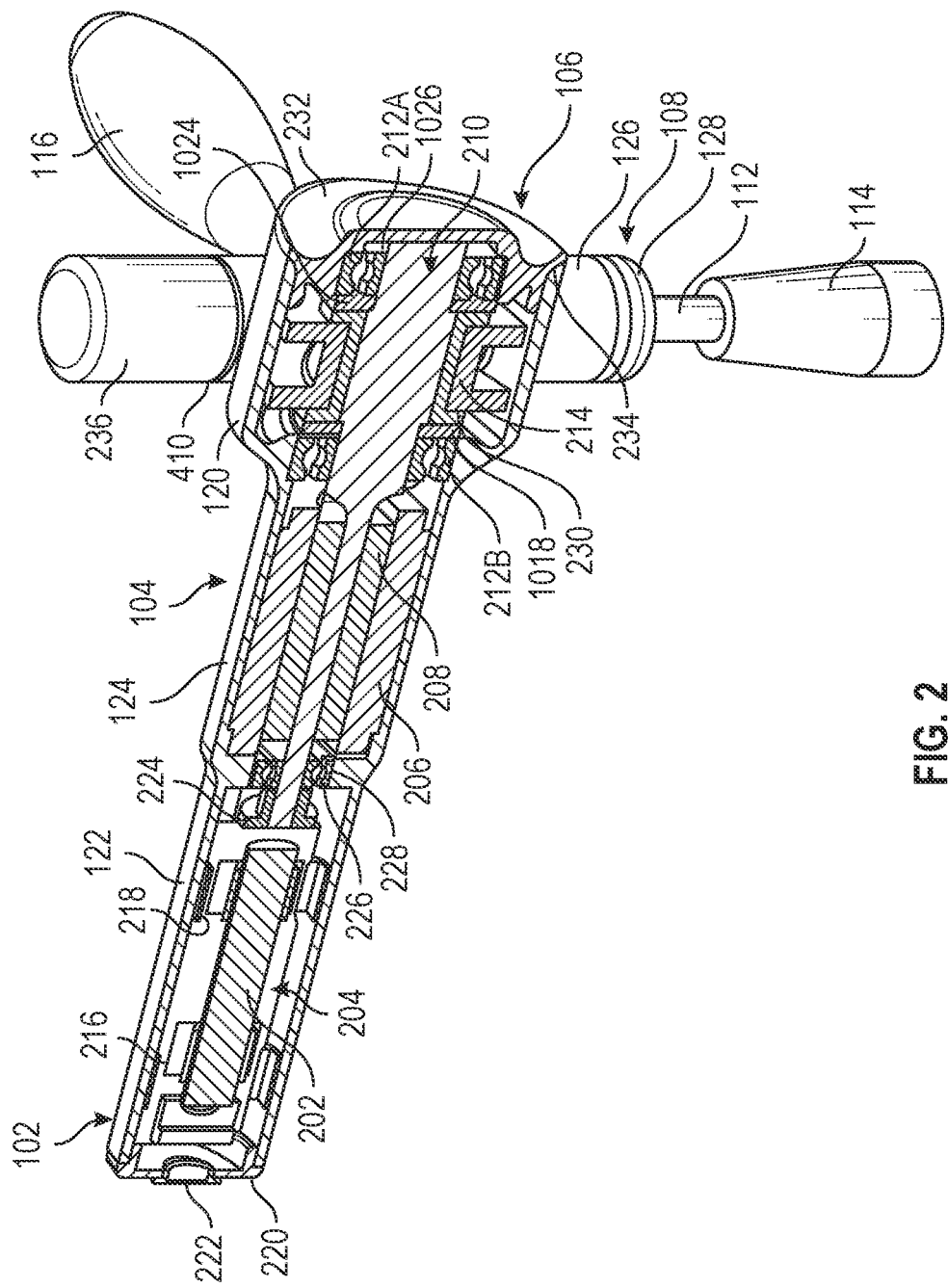
FIG. 2 shows a side isometric cutaway view of a rotary electric surgical hammer impact tool in accordance with at least one example of this disclosure.

Turning now to the figures, FIG. 1 shows an isometric view of rotary electric surgical hammer impact tool 100 consistent with at least one example of this disclosure. With reference to FIGS. 1 and 2, the rotary electric surgical hammer impact tool 100 can include a handle housing 102, which inside can contain a battery pack 202 and control electronics 204. As disclosed herein, a user interface, which can be a mechanical switch or voice activated controls as described in accordance with FIG. 3 below. A motor housing 104 can contain an electric motor stator 206, which can be a frameless motor with coils attached to the inside of the housing 104 and a rotor 208 mounted on a shaft 210 that extends through to a hammer head housing 106, sometimes abbreviated as HHH, in which main bearings 212 (labeled individually as bears 212A and 212B) are supported and a disk hammer element 214, sometimes abbreviated as DHE, is located. Tangentially attached to the disk hammer element 214 can be a tool holder element 108, sometimes abbreviated as THE, which can contain a tool post 110 with its lower shaft 112 and tool holder 114 at its end for holding a tool such as a broach (not shown).

A side handle 116 can thread into a boss 118 and allow a user to better grip and control the rotary electric surgical hammer impact tool 100. A similar boss could be located on a housing 120 opposite, so a left handed user could then grip the side handle 116 with his or her right hand.

Figure 3:
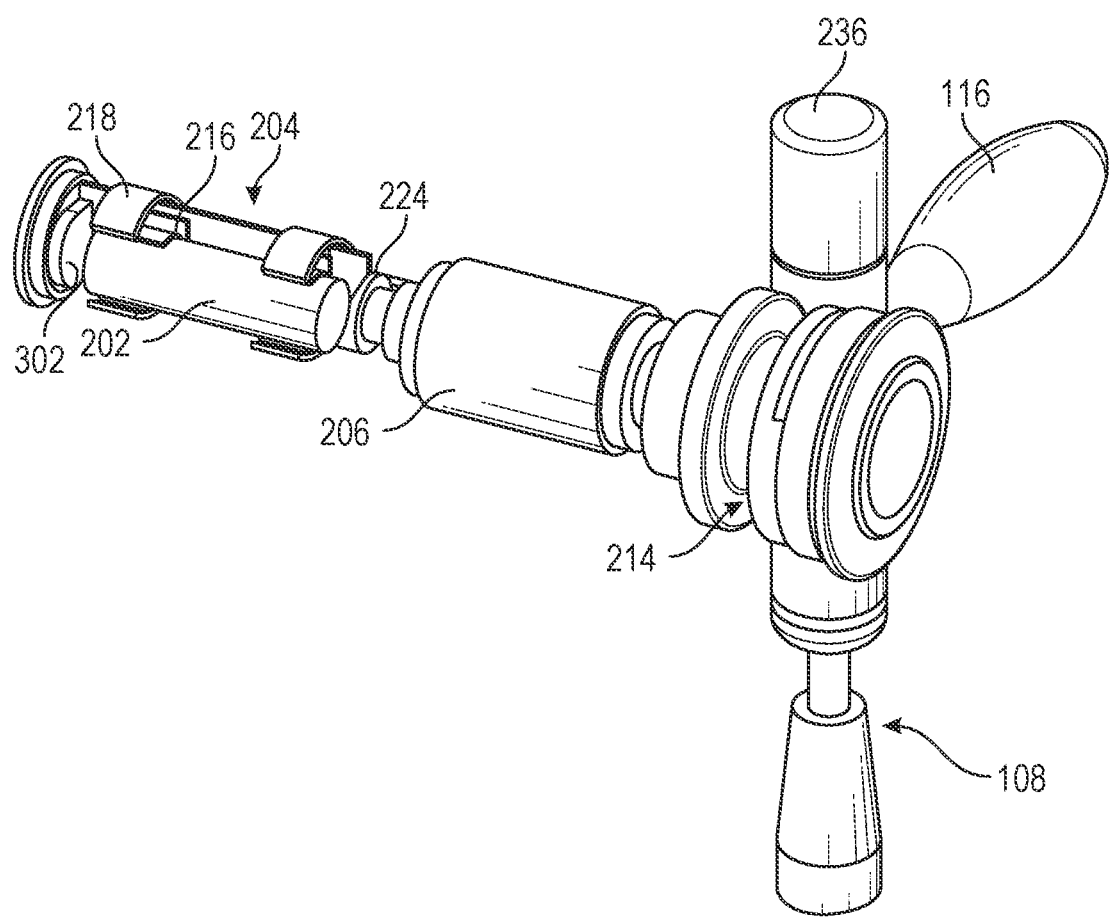
FIG. 3 shows a side isometric view of interior elements of a rotary electric surgical hammer impact tool in accordance with at least one example of this disclosure.
Figure 4:
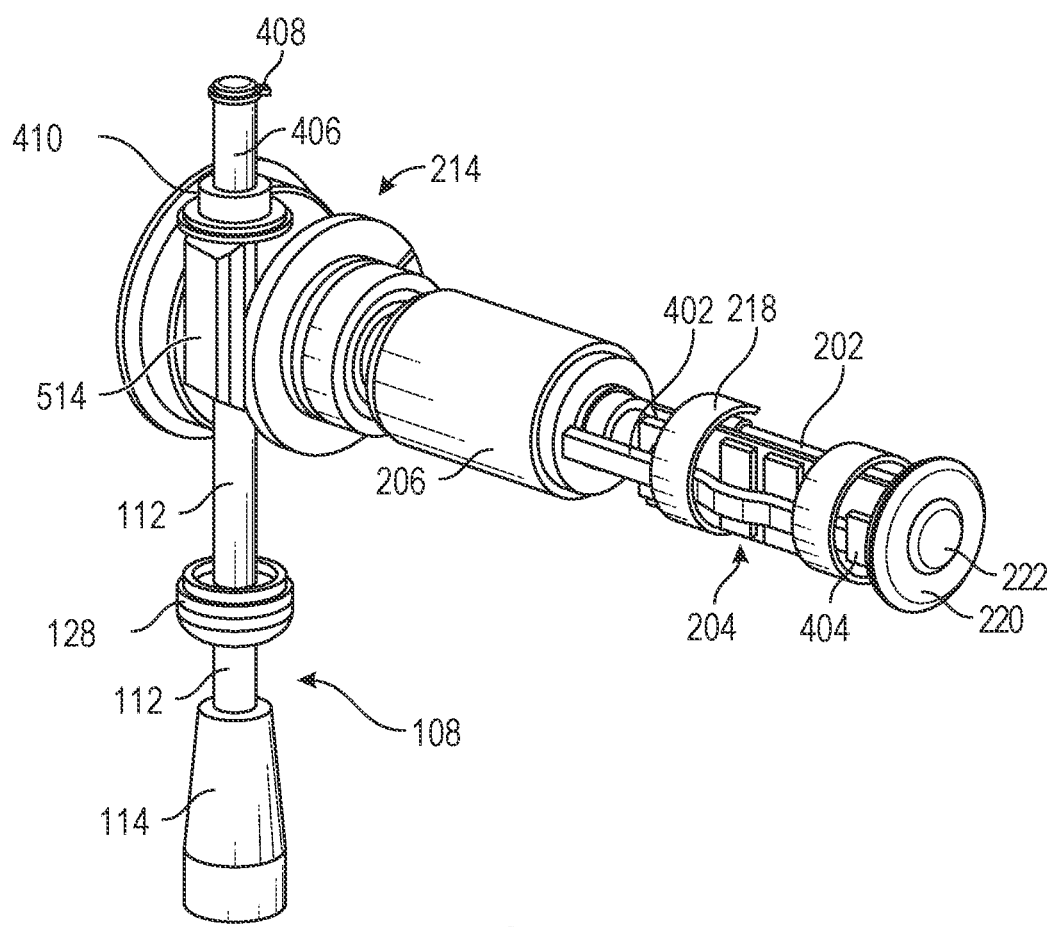
FIG. 4 shows another side isometric view of interior elements of a rotary electric surgical hammer impact tool in accordance with at least one example of this disclosure.

FIG. 2 shows a side isometric cutaway view of the rotary electric surgical hammer impact tool 100, and FIGS. 3 and 4 show side isometric views of interior elements of the rotary electric surgical hammer impact tool 100 with outer structural housings removed. The handle housing 102 can have an outer structure 122 that houses the battery pack 202, which can be held to the circuit board 204 by clips 216, as shown in FIG. 3. The circuit board 204 can also be held, by clips 218, to the inside of the structure 122. An end cap 220 can may be threaded for mounting in the end of outer structure 122. A microphone cover 222 can be located in the center of the end cap where it is not likely to be occluded and would be well placed to transmit voice commands from the user to be received by a microphone/speaker 302.

FIG. 4 shows a motor cable 402 leading from the motor stator 206 to a connector 404 on the circuit board 204 near its distal end so it can be more readily snapped into place during assembly. The battery pack 202 can be a stack of coin cells in a housing with the overall energy required and voltage, which may be about 40 volts DC, to enable the motor to spin at up to several thousand rpms.

Many different users have many different hand types and operating a power tool in an operating theatre with gloves can be cumbersome so a conventional switch or power adjust knob can be undesirable. Accordingly, voice control can be used as disclosed herein. The rotary electric surgical hammer impact tool 100 can have the microphone 302 connected to the circuit board 204, which can be used to control the current to the coils 206. The microphone 204 can allow the user to speak commands as they are using the rotary electric surgical hammer impact tool 100 such as "less force," "more force," "faster" "slower," etc. and it will be understood that the rotary electric surgical hammer impact tool 100 can be trained by the user to meet their needs and style of use.

The motor housing 104 can have an outer structure 124, which can be integral with the handle structure 122, but the handle structure 122 can be located elsewhere and have a D-handle configuration. The motor stator 206 and coils 208 can be a frameless motor, so the stator 206 can be bonded in place within the outer structure 124 for securement and good heat transfer. If the motor stator 206 could get too warm, then the outside of the structures 122 and 124 can be rubber coated and/or insulated with an ergonomic grip. The motor coils 208, such as a magnetic rotor for a DC brushless motor, can be bonded to a shaft portion 1002 (see FIG. 10B) of the shaft 210. As shown in FIGS. 2 and 11A, a magnetic encoder disk 224 can be attached to an end 1005 of the shaft 210 and a sensor on the circuit board 204 can sense the rotation of the shaft 210.

Figure 10A:
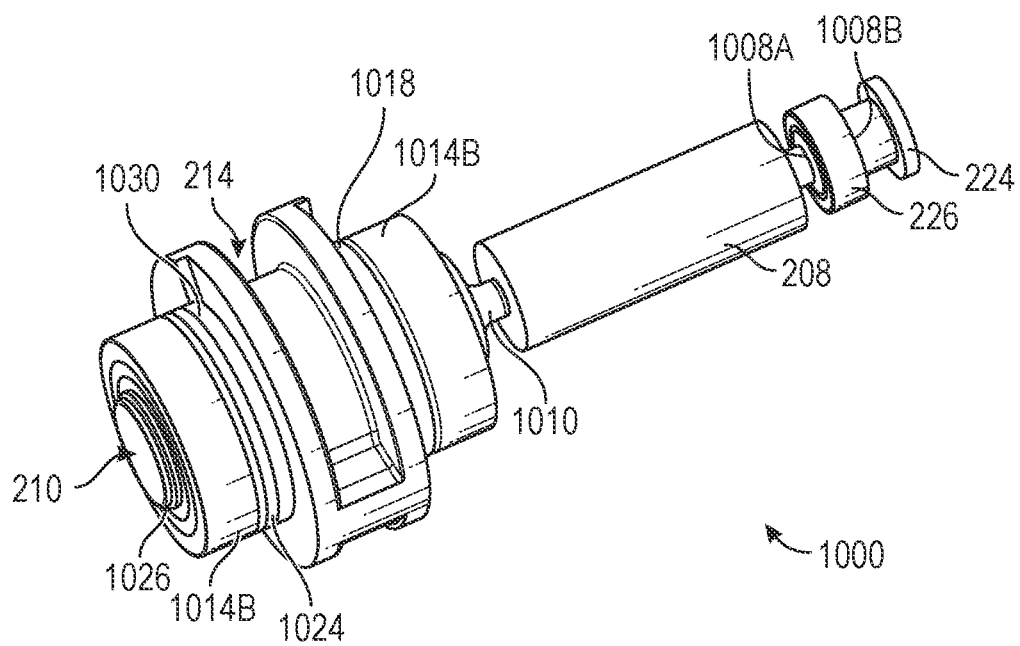
FIGS. 10A and 10B show isometric views of a polymer torque interface element in accordance with at least one example of this disclosure.
Figure 10B:
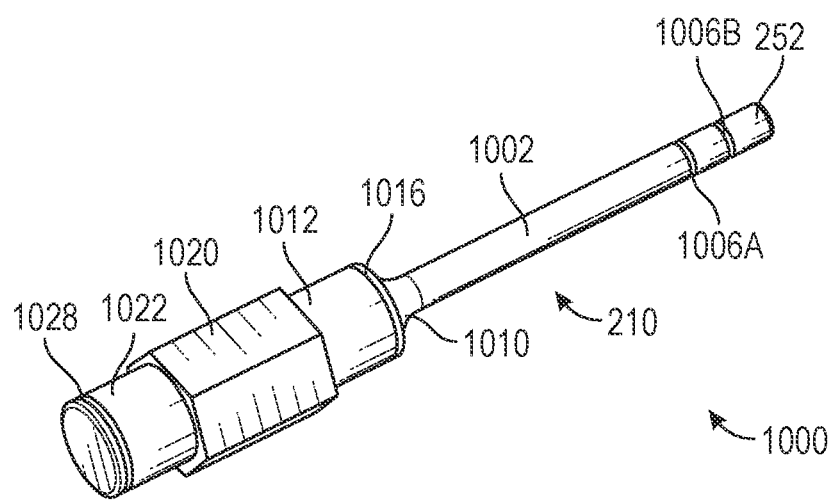

With reference to FIGS. 10A and 10B details of the rotor system 1000 are shown, which can be built as a subassembly, precisely balanced and readied for insertion into the housings 104 and 106. As shown in FIG. JOB, the central main shaft 210 can be manufactured as a single element, which can start from hexagon stock held in a precision collet and then turned or ground. Starting at the distal end, which is the end nearest the handle housing 102, the end 1004 can have the encoder 224, such as a magnetic, encoder, attached for feedback on the position of the coils 208 to the controller 204. Snap ring grooves 1006 (labeled individually as snap ring grooves 1006A and 1006B) can be sized to receive snap rings 1008 (labeled individually as snap rings 1008A and 1008B) to axially constrain outrigger support bearing 226, which can be constrained radially in the housing 120 by an end flange 228. The shaft portion 1002 can be for motor rotor 208, which can be bonded to the shaft portion 1002, such as with an adhesive, welding, etc.

The shaft portion 1002 for the motor rotor 208 can utilize, for example, a MOOG DB-1500-R motor that is only ¼" diameter, and while it can handle the torque and inertial loads, stress concentrations can be minimized and hence the full radius 1010 transition to the diameter 1012 of the shaft at 0.750" supported by the main support bearings 1014 (labeled individually as bearings 1014A and 1014B), which can absorb the force of impact. A snap ring groove 1016 can be sized to receive a snap ring to axially constrain bearings on the shaft when it is installed after spacer flange hub washer 1018 with 0.750" bore is installed. This washer 1018 can have on the side facing the bearing 1014A an outer diameter no larger than the bearing's inner ring outside diameter, and then a step to the larger diameter needed to support an axial face 1102 (see FIG. 11) of the hexagonal torque interface element 230. Shaft section 1020 of main shaft 210 can be hexagonal for transition of torque from the motor 206, 208 through the resilient polymer hexagonal torque interface element 230's, sometimes abbreviated TIE, hexagonal bore 1104 (see FIG. 11) in the center section 1106, which can be axially constrained by the spacer flange washer 1018 that can prevent rubbing on the bearing's non rotting outer race. The torque interface element 230 can provide torque transmission with some torsional compliance without energy loss if it is made of a low loss polymer such as BUNA N rubber or a cast polyurethane. This can help to reduce shock on the rotor system 208 while extending the period of the impulse force on the tool holder element 108.

Continuing to the proximal end, the shaft can step down to 0.750" diameter 1022 for the second spacer flange hub washer 1024 to press against the proximal face 1102 of the torque interface element 230. Next support bearing 1014A cane be held axially in place by snap ring 1026 in a groove 1028.

Figure 5:
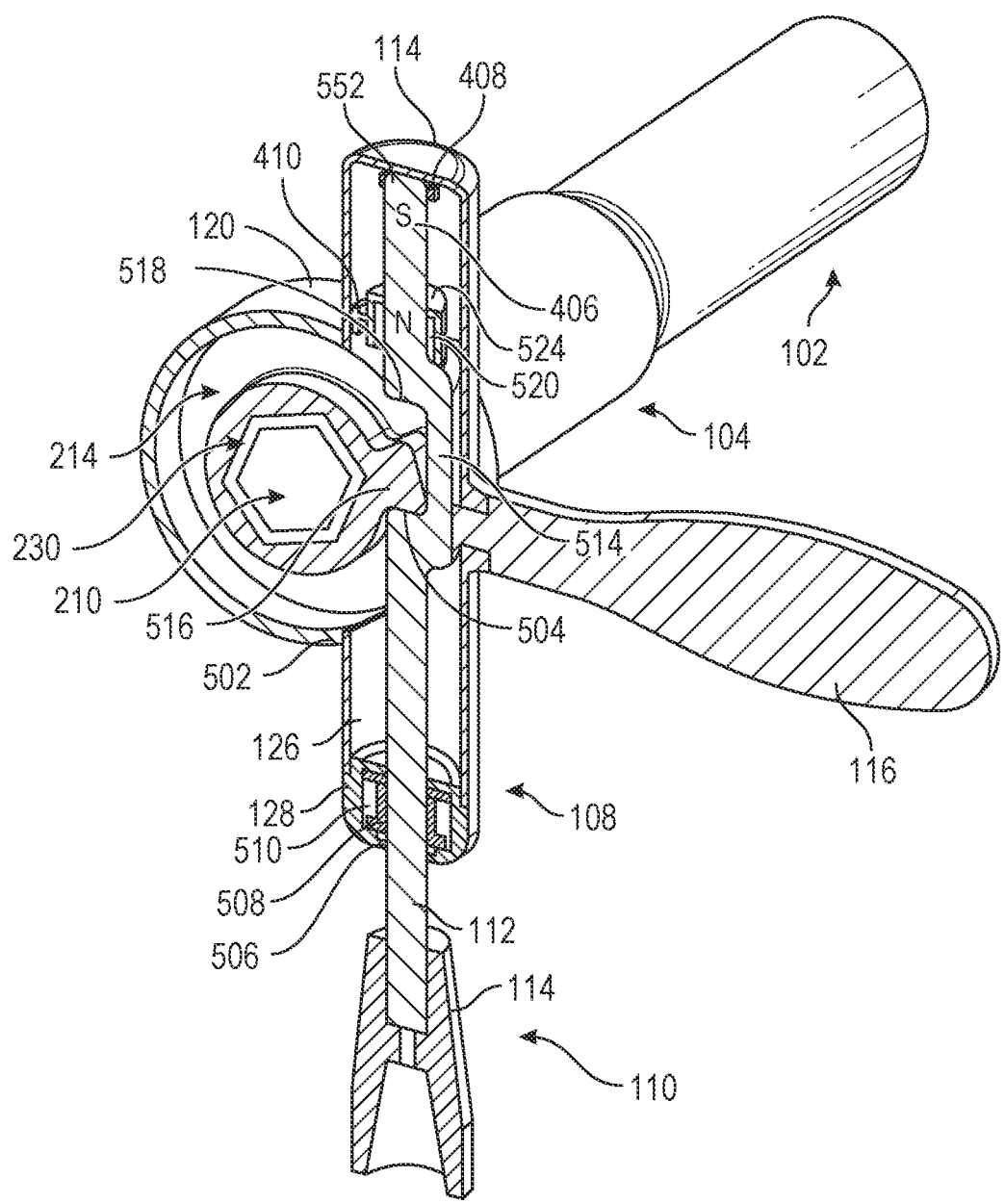
FIG. 5 shows a front isometric cutaway view of a rotary electric surgical hammer impact tool in accordance with at least one example of this disclosure.

The outer structure 120 can have a precision bore for receiving the main bearing 212B and an end cap 232 with a precision bore for the main beating 212A. Concentricity and squareness can be obtained via a tapered interface 234. The end cap 232 can be used so the disk hammer element 214 can be inserted. As can be seen in FIG. 5, the outer housing 120 can have a tangential bore 502 in it for the outer housing 126 of the tool holder element 108.

Figure 6:
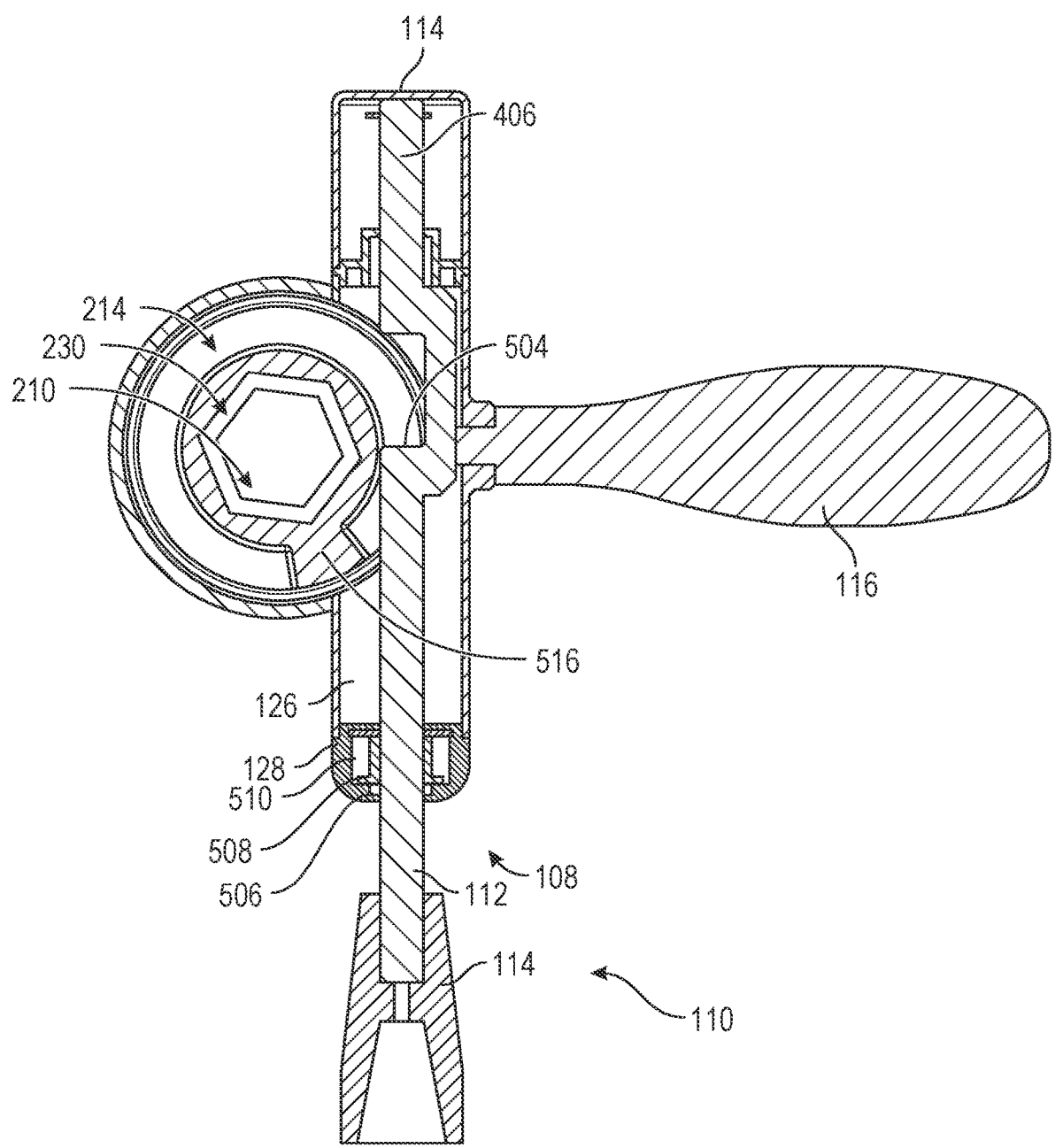
FIG. 6 shows a front cutaway view of a rotary electric surgical hammer impact tool in accordance with at least one example of this disclosure.
Figure 7:
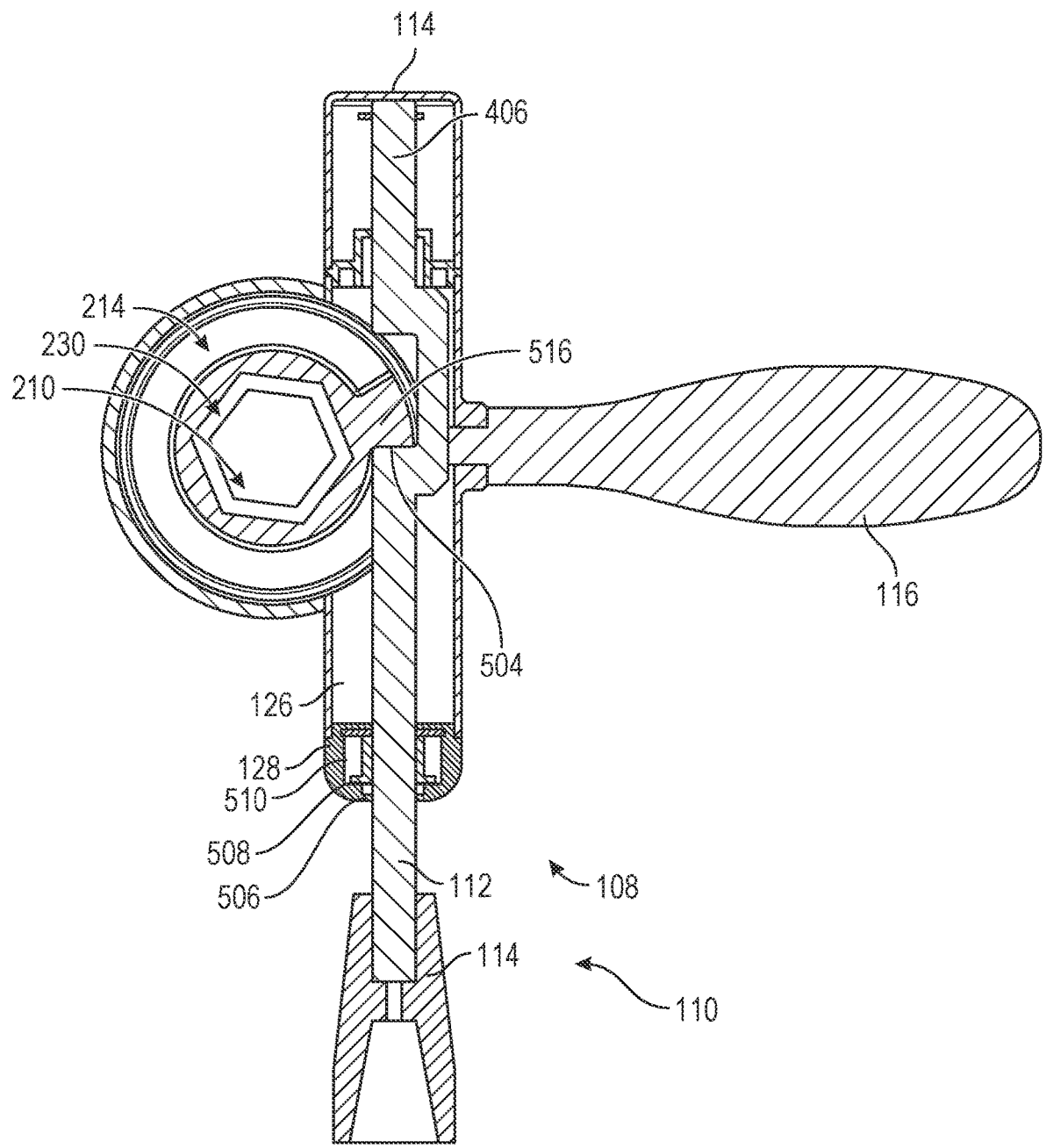
FIG. 7 shows a front cutaway view of a rotary electric surgical hammer impact tool in accordance with at least one example of this disclosure.

FIGS. 5 and 7 show cutaway views the rotary electric surgical hammer impact tool 100 in an impact tool driving position and FIG. 6 shows the rotary electric surgical hammer impact tool 100 ready to accelerate the disk hammer element 214 clockwise (as shown) to cause the impact. Inside outer housing 120 the disk hammer element 214 can be held to the shaft 210 by the hexagonal torque interface element 230 show in FIG. 11) to cause a radial impact face 516 to impact face 504 on the distal end of shaft 112 of the tool holder element 110 to enable a tool held in it to do useful work, when a user has pushed the rotary electric surgical hammer impact tool 100 forward to engage with the part on which it is intended to do work (e.g., bone).

The axial position of the impact face 516 can be set by the end of distal shaft of the tool holder element 110 contacting the inside of cap 236, or alternatively, a flange on the proximal shaft 112 can contact the outside proximal surface of proximal end flange 128. The tool post 110 can be forged and then machined to final shape, where the end shaft regions 406 and shaft 112 can be ground for precise fit and smoothness to yield longer bearing life.

The shaft 112 can be sealed with a simple O-ring or a Quad-ring such as a ring 506 in a groove in the proximal end flange 128 that can be threadedly connected to outer housing 126. Consistent with embodiments disclosed herein, a bellows seal can be used that allows for effectively unrestrained axial motion, or a metal bellows can provide a slight spring bias, while providing a hermetic seal.

A bellows for sterilization purposes, can allow gas inside the rotary electric surgical hammer impact tool 100 to expand and push out as needed by deflecting the bellows. The shaft 112 can slide through a bearing bushing 508, which can be a dry running low friction polymer such as Rulon. The proximal end flange 128 can be held in a housing 510 and pressed on the flange of the bushing 508 to restrain it. Alternatively, a simple cylindrical busing can be held in place with a snap ring.

As shown in FIG. 5, the distal shaft 512 can be connected to the proximal end if the shaft 112 by a C-shaped structure 514 that can allow the radial impact face 516 to pass through to impact either face 504 for driving the tool, or if the user pulls back on the rotary electric surgical hammer impact tool 100 the tool holder element 108 can slide down to be stopped by the snap ring 408 coming in contact with the distal end of structure 410. When the disk hammer element 214 rotates counterclockwise, the radial impact face 516 can impact face 518 to retract the tool holder element 108.

Figure 13A:
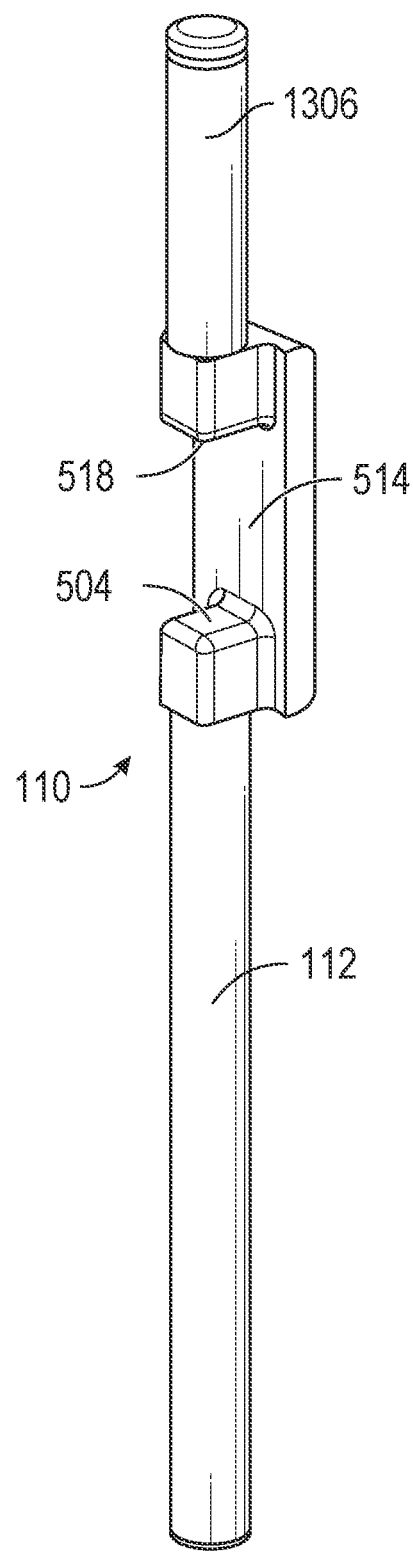
FIG. 13A shows an isometric view of a tool holder element in accordance with at least one example of this disclosure.
Figure 13B:
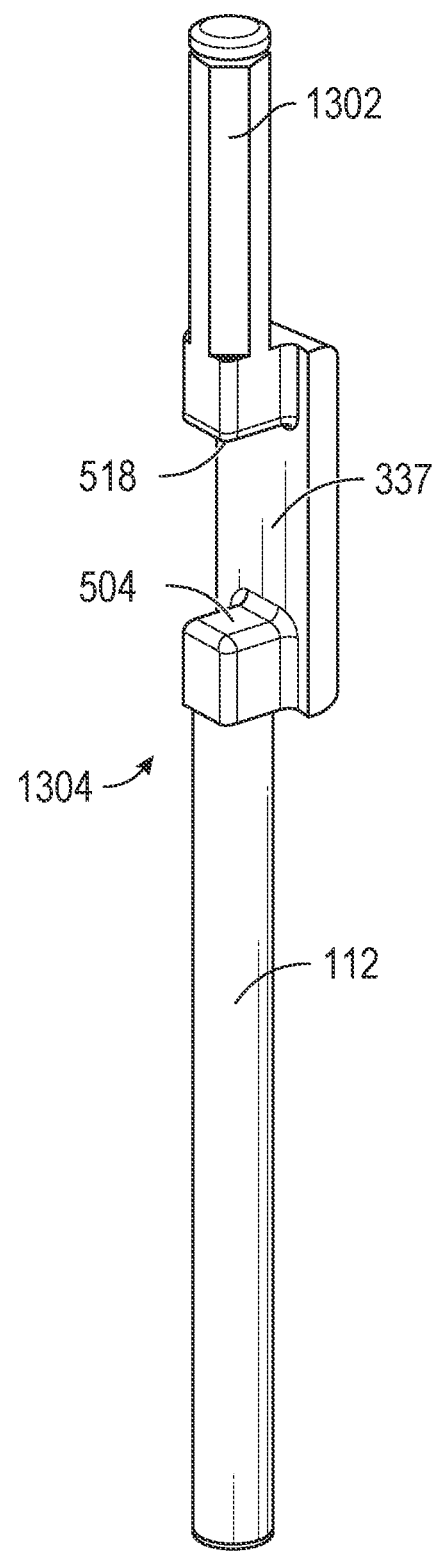
FIG. 13B shows an isometric view of a tool holder element in accordance with at least one example of this disclosure.

As shown in FIG. 13B, a distal shaft 1302 can have a hexagonal cross section to constrain rotation of a tool post 1304. The distal shaft 1302 may not transfer an impact force and can support the distal end of the tool holder element 108 so the bearings 520 and 508 can provide moment stiffness to the tool holder element 108. The core of the shaft 515 can thus be drilled out and a rod magnet inserted to create a north pole and a south pole 522, which may be sensed by a Hall effect sensor 524 to enable the microcontroller on circuit board 204 to know the tool holder element 108 is positioned in the proximal position for a drive impact or distally for a retract strike. Thus, north pole and a south pole 522 and the Hall effect sensor 524 can cooperate to prevent the disk hammer element 214 from rotating and striking the tool holder element 108 if it is in the wrong position.

Figure 8:
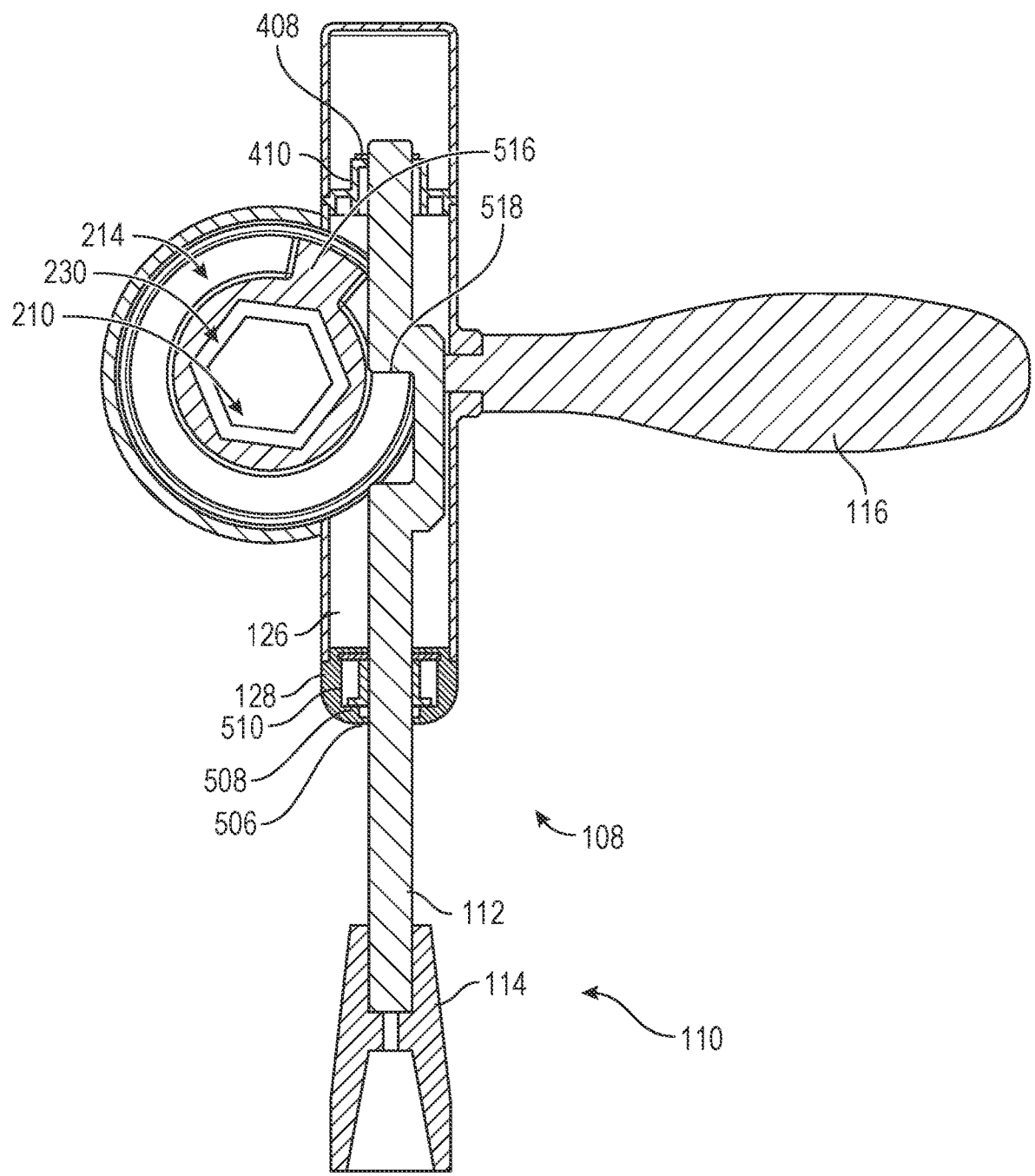
FIG. 8 shows a front cutaway view of a rotary electric surgical hammer impact tool in accordance with at least one example of this disclosure.
Figure 9:
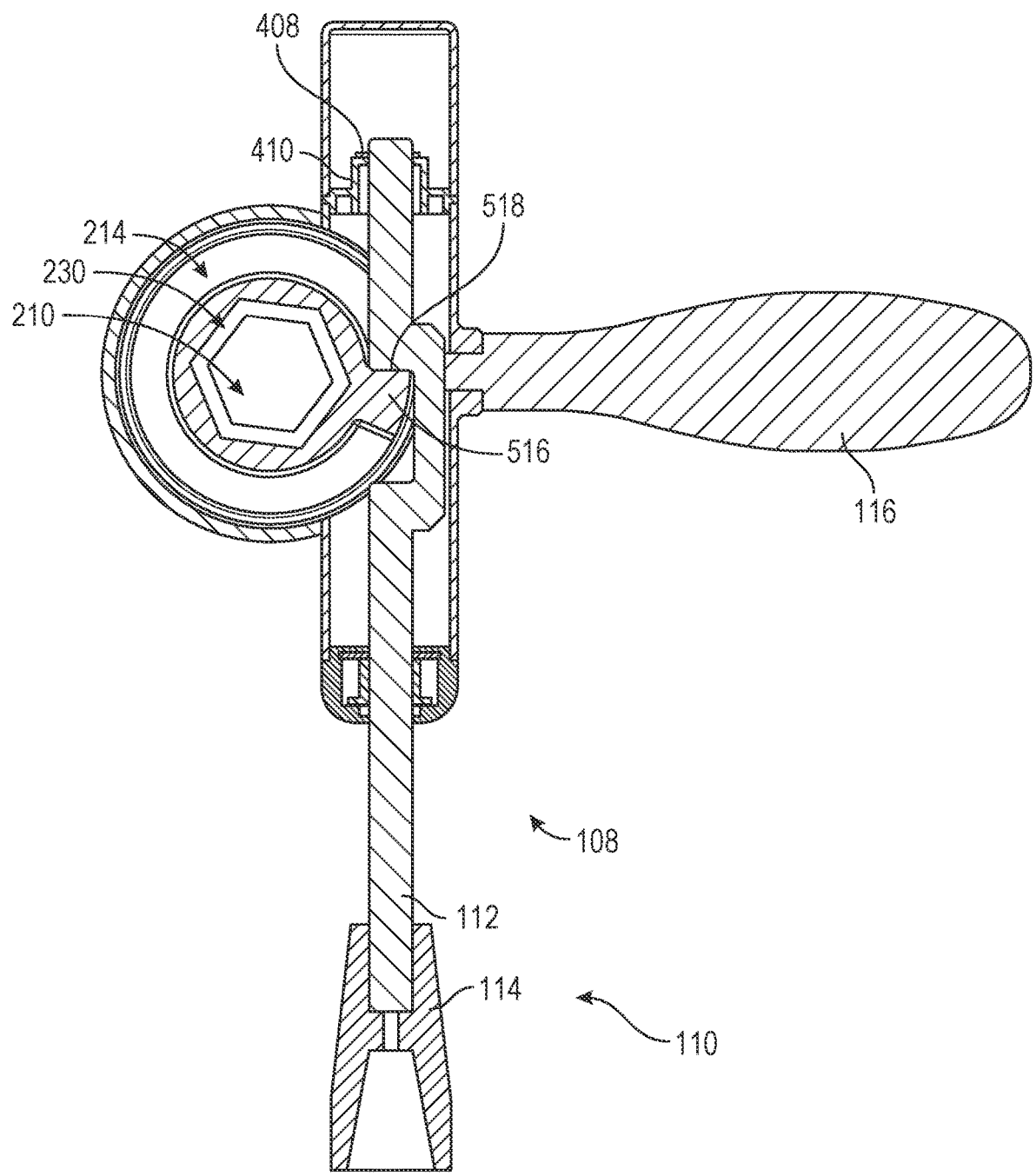
FIG. 9 shows a front cutaway view of a rotary electric surgical hammer impact tool in accordance with at least one example of this disclosure.

FIGS. 8 and 9 show cutaway views of the retraction process where the disk hammer element 214 is first rotated clockwise, it is then be accelerated counterclockwise so the radial impact face 516 impacts the retraction impact face 518. The user can have pulled back in the distal direction on the rotary electric surgical hammer impact tool 100 such that the tool holder element 108 can slide in its bearings until the snap ring 408 makes contact with the back of distal end flange 410. This properly positions the retraction impact face 518 to be impacted by the radial impact face 516 in a counterclockwise rotation mode.

FIG. 10A shows an isometric view of the rotor system elements assembly 1000, where the elements can all be assembled and then dynamically balanced using the support bearings 212A, 212B, and 226 including any shaft straightening required to ensure the bearings 212A, 212B, and 226 are all concentric. FIG. 10B shows an isometric view of the shaft 210 upon which the elements are mounted. The rotor 208 of the motor can be attached to the rotor shaft section 1002 with high precision and have ability to transmit the full torque of the motor. It can also resist torsional impact loads. This attachment can be by shrink fitting or via a thin film adhesive that can be used to bond the rotor 208 to the shaft 1002.

The rotary inertia of the disk hammer element 214 can be the largest, but that of the motor rotor 208 and shaft 1002 can also be significant. Combined they can deliver the energy to the impact. A low-loss factor hard rubber element 1030 between the disk hammer element 214 and the hexagonal end of the rotor shaft 1002, such that when the impact occurs, the motor rotor 208 can decelerate more slowly and less stress placed on the magnets and on the smaller diameter portion of the rotor shaft 210 onto which the motor rotor 208 can be attached. This also has the benefit of the tool holder element 108 receiving an initial blow with a trailing high force. The initial spike can cause the cutting action to initiate followed by a period of continue force to further advance the tool and complete the cut.

Figure 11:
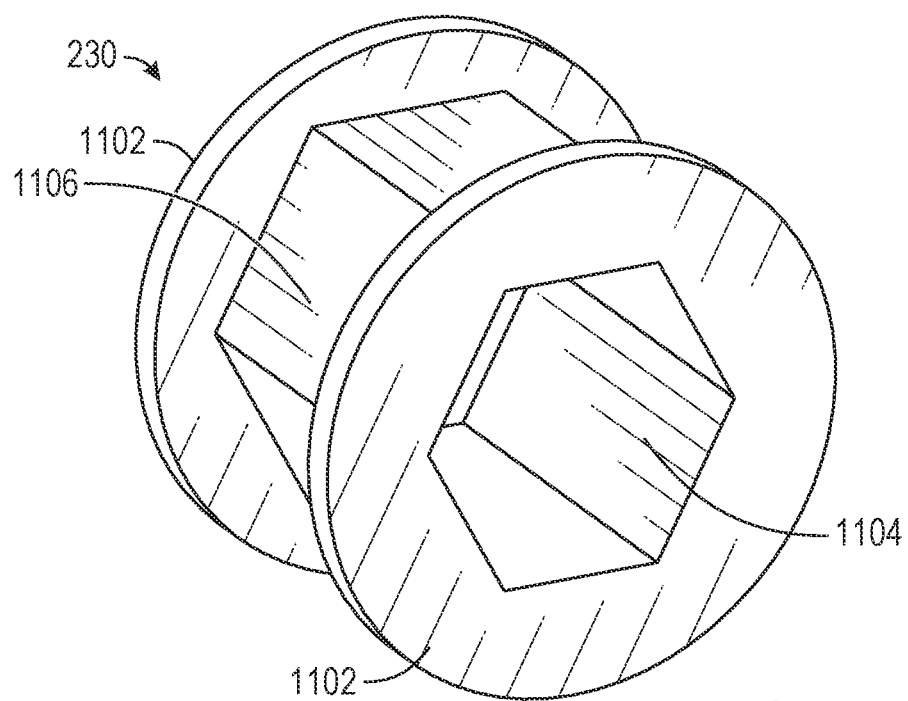
FIG. 11 shows an isometric view of a disk hammer element in accordance with at least one example of this disclosure.

FIG. 11 shows a resilient torque interface element 230 that fits in the hexagonal bore 1204 of the disk hammer element 214. The torque interface element 230 can be made from a resilient low loss polymer, such as a polyurethane. Polyurethanes can be used because they can resiliently tolerate shock loads and not dissipate energy as heat (i.e., they can have a low loss factor) and are wear resistant in this sort of coupling loading. The use of a torque interface element 230 can help to reduce the shock load on the motor rotor 208 and its bonded-in place permanent magnets. By reducing the shock load, this lengthens the energy transfer period and also helps create the dead blow hammer affect that may be desirable for operating the rotary electric surgical hammer impact tool 100 in a more effective way for cutting operations.

Figure 12:
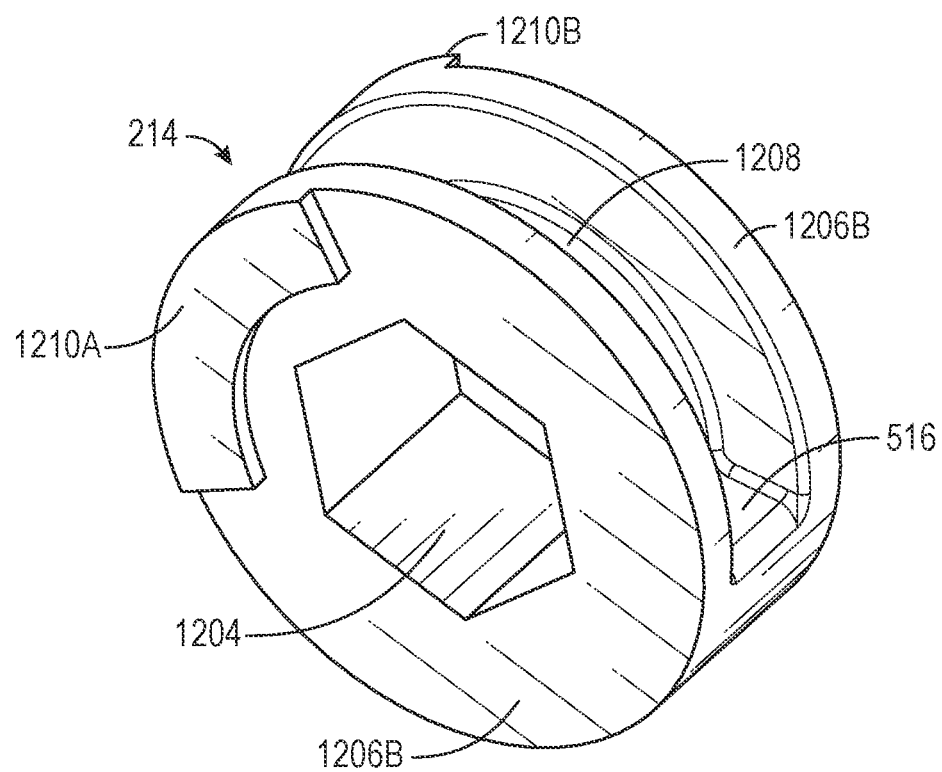
FIG. 12 shows an isometric view of a disk hammer element in accordance with at least one example of this disclosure.

As shown in FIG. 12, the disk hammer element 214 can have outer flanges 1206 (labeled individually as outer flanges 1206A and 1206B) and an inner joining structure 1208 integral with the flanges 1206. A hexagonal opening 1204 can be provided in the disk hammer element 214 for receiving torque interface element 230. The disk hammer element 214 can have a semi-circular outside diameter from which projects radially the radial impact face 1202, which is the structure that impacts the impact surfaces of the tool holder element 108 to drive the tool in or retract it. The radial impact face 1202 can be integrally formed with the outer flanges 1206 and inner joining structure 1208 and thus can be fully supported on three sides. Because the rotational speeds can get to several thousand RPM, the disk hammer element 214 can be dynamically balanced and thus balance segments 1210 (labeled individually as balance segments 1210A and 1210B can be machined integral with the disk hammer element 214 structure.

FIG. 13A shows an isometric view of the tool post 110 of the tool holder element 108 who's upper (distal) shaft 1306 is shown as being round. To prevent rotation, shaft 1302 can be hexagonal as shown in FIG. 13B and move in a corresponding hexagonal linear bearing bushing in end flange 410. The upper shaft can be housed and thus does not need to be sealed to the outside world. For a fast, hard crisp blow though, hard steel on hard steel can be used for the disk hammer element 214.

Figure 14:
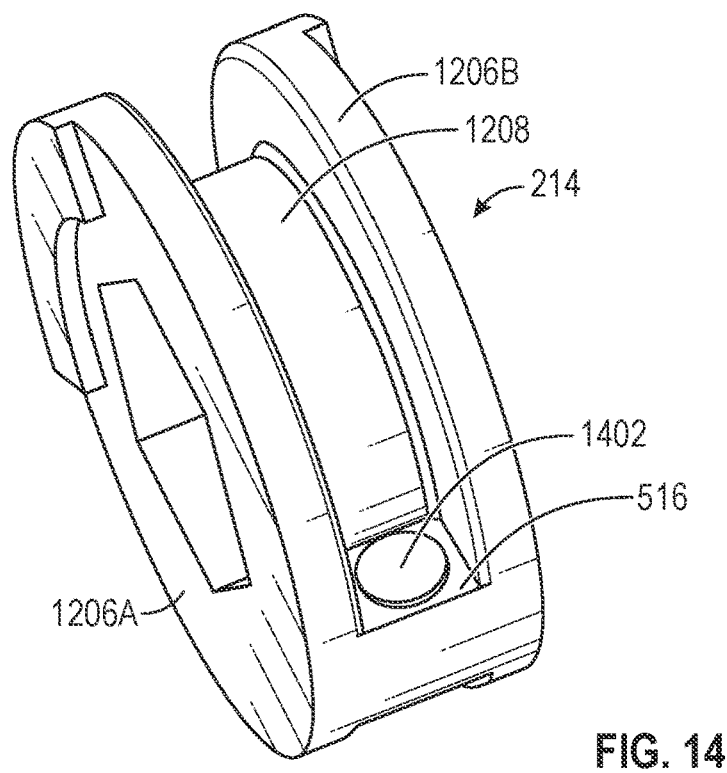
FIG. 14 shows an isometric view of a disk hammer element in accordance with at least one example of this disclosure.

FIG. 14 shows the disk hammer element 214 for softening and extending the impact. FIG. 14 shows an isometric view of the disk hammer element 214 with a dead blow interface element 1402 in the radial impact face 1202. The dead blow interface element 1402 can be modular and replaceable, here shown in the form of a button that would be pressed into a pocket on its surface, and can be made from different materials or composites such that it can be configured from hard steel to deliver very high force sharp short duration impacts, or from a softer material such as a polymer to deliver a lower longer duration force akin to that provided by a dead blow hammer or a lignum vitae wood hammer. is the polymer can be a hard polyurethane, such as a hot cast polyurethane. The particular size (e.g., diameter and length) and material chosen for the dead blow interface element 1402 can be determined by experimentation until the "feel" is good for users, and it can be quantified with accelerometer measurements made as the rotary electric surgical hammer impact tool 100 is used and user feedback recorded.

Figure 15A:
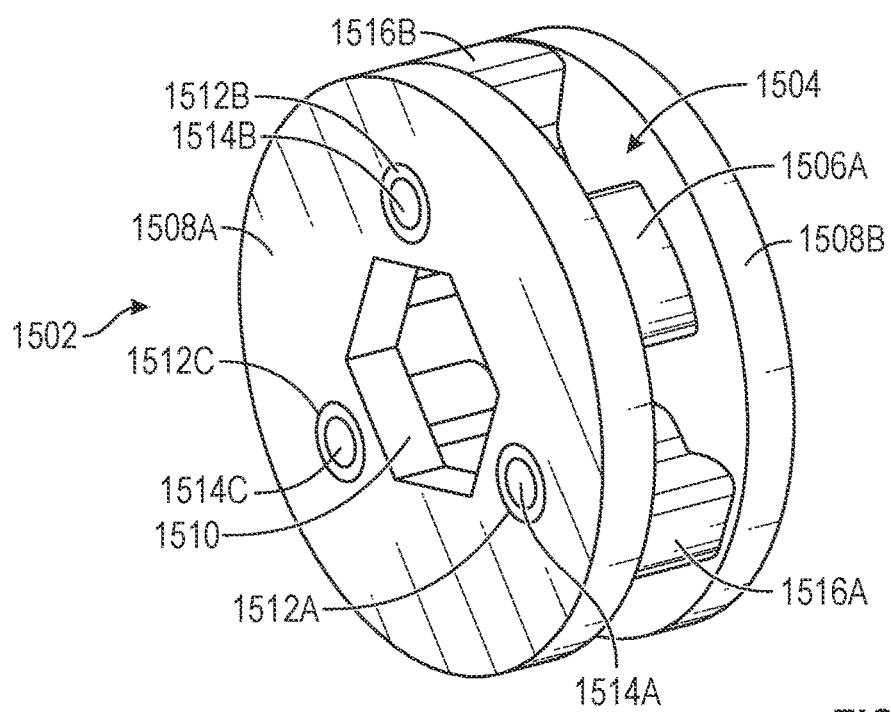
FIG. 15A shows an isometric view of a disk hammer element in accordance with at least one example of this disclosure.
Figure 15B:
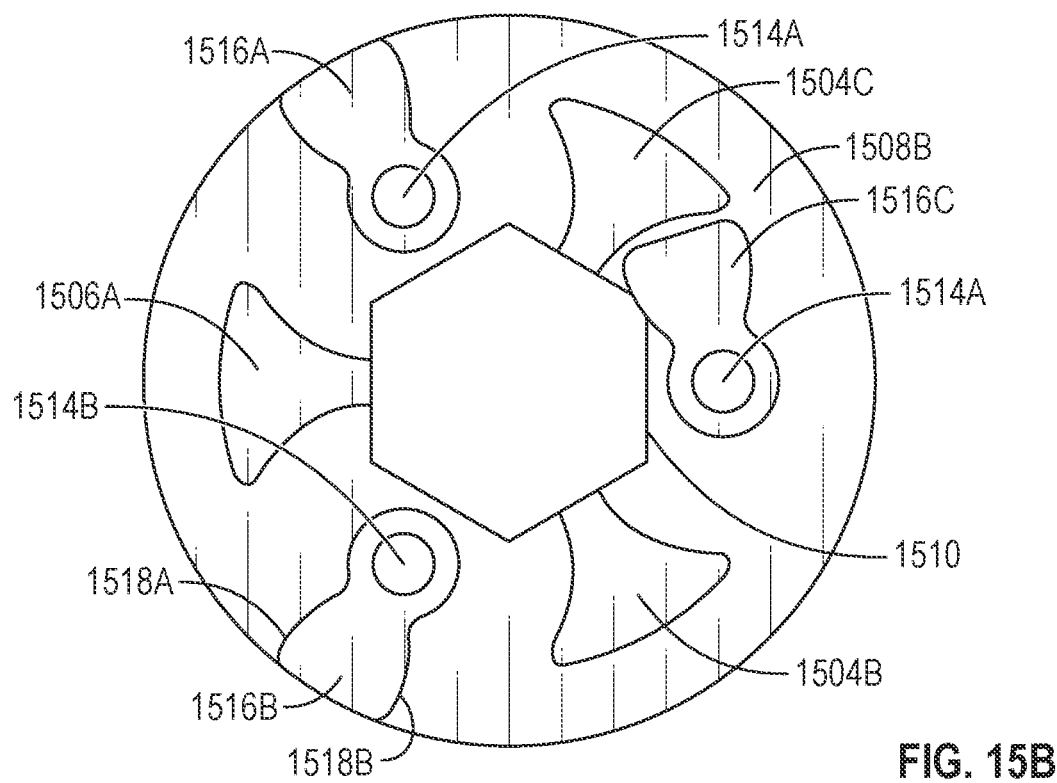
FIG. 15B shows a side cutaway view of a disk hammer element in accordance with at least one example of this disclosure.
Figure 15C:
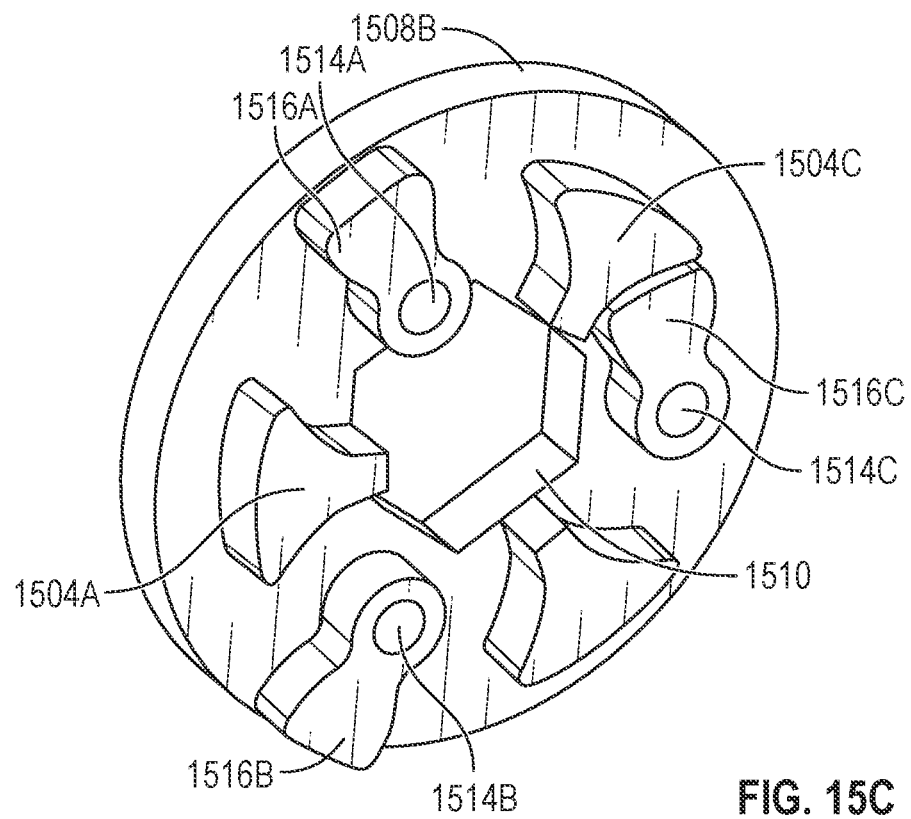
FIG. 15C shows a cutaway isometric view of a disk hammer element in accordance with at least one example of this disclosure.

As shown FIGS. 15A, 15B, and 15C, the disk hammer element 1502 can have cutouts in the inner joining structure 1504 to form connections 1506 (labeled individually as connections 1506A, 1506B, and 1506C) between side plates 1508 (labeled individually as side plates 1508A and 1508B), which can have a hexagon center bore 1510.

The side plates can contain holes for pairs of bushing bearings 1512 (labeled individually as busing bearings (1512A, 1512B, and 1512C), which can be made of a low friction dry running sterilizable plastic such as Rulon. Shafts 1514 (labeled individually as shafts 1514A, 1514B, and 1514C) can be supported by the respective sets of bushings and support swinging hammers 1516 (labeled individually as swinging hammers 1516A, 1516B, and 1516C). The disk hammer element 1502 can rotate continuously clockwise when driving or counterclockwise when retracting the tool holder element 108. This disk hammer element 1502 can be coupled to the shaft 210 by the resilient torque interface element 1030.

As shown in FIGS. 15B and 15C one swinging hammers 1516, such as swinging hammer 1516C, can have swung back, which would happen after striking the tool holder element 110. The swinging hammers 1516 can have arcuate faces such as faces 1518 (labeled individually as faces 1518A and 1518B) that can provide a rolling motion against the impact faces 504 and 518 on the tool holder element 110 for driving and retracting the rotary electric surgical hammer impact tool 100 respectively. After impacting and swinging back and clearing the tool holder element 110, the swinging hammers 1516 can impact the exposed free surface of a portion of the torque interface element 230, which can help it with centrifugal force to swing back out pointing in the radial direction ready for the next impact. The hammers' mass and inertia can be small compared to the disk hammer element 1502, but the higher frequency and the hammers 1516 can help make up for this. In addition, the swinging hammers 1516 can be made from a high-density material like tungsten carbide, which is about twice the density of steel.

Figure 16A:
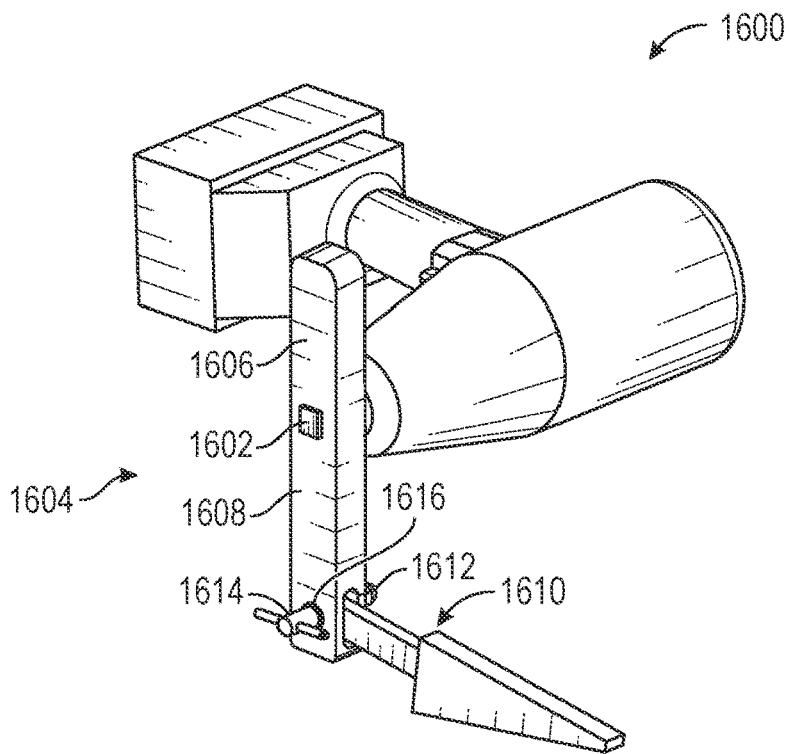
FIG. 16A shows a center of percussion arm rotary system in accordance with at least one example of this disclosure.

As disclosed herein, a center of percussion arm rotary systems can use the principle of rotary impact to create linear driving force by applying small rotary motion impacts in the vicinity of the distal end of a lever arm to drive a tool connected by a pivot at the center of percussion of the arm, including the mass of the tool, to achieve in effect linear impact motion at the tool without the user feeling the impact force. This can be accomplished as shown in FIG. 16A with a system 1600 that can include a battery power impact wrench. The mechanism can have a control system, such as a controller disclosed herein, that monitors the rotation of a square drive output shaft 1602 so it does not spin more than about 30 degrees. Attached to the system 1600 can be a center-of-percussion tool-arm 1604. This arm can have a distal end 1606 and a proximal end 1608 whose length and mass can be in proportion to the attachment location and mass of a tool 1610. The tool 1610 can fit in a slot 1216 and can be held to the arm 1604 by a quick release pin 1614 that can slide through a hole 1616 in the arm 1604. The tool 1610 can have a corresponding hole in its shank to receive the pin 1614. The slot 1612 can allow the tool 1610 to pivot about the pin 1614.

The dimensions and mass of the arm sections 1606 and 1608 in proportion of the tool 1610 can enable the user to actuate the device 1600 while pushing the tool 1610 into the bone to carve a channel. For example, the user can resist the impact torque, much of which is taken up by the inertia of the device 1600 itself just as with a normal impact wrench. The user may not feel the linear impact force of the tool 1610 driving into the bone because arm proportions place the impact force at the center of percussion of the arm 1604. The torque through the square drive 403 instead of loosening a nut, for example if used as an impact wrench, can be turned into an axial force on the tool 1610 through the pin 1614.

Figure 16B:
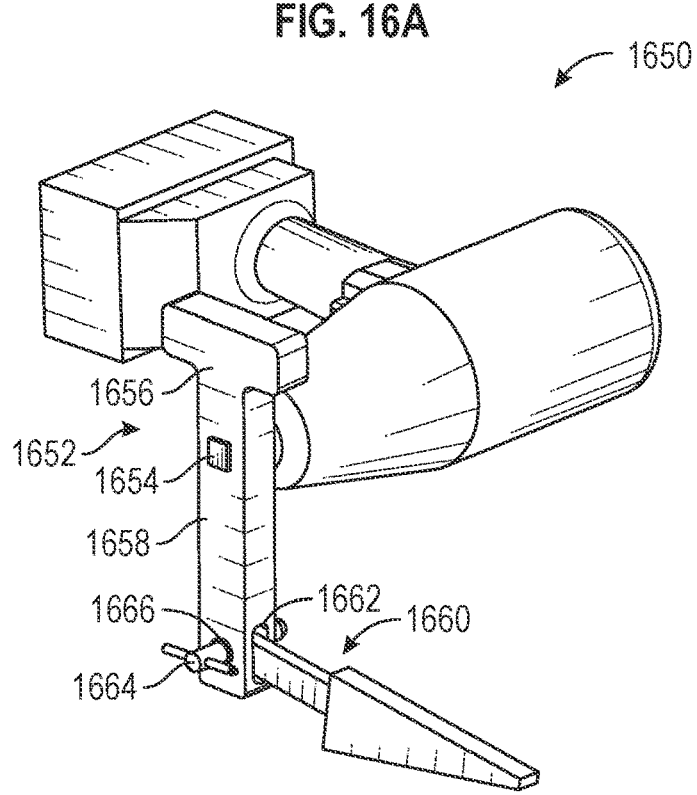
FIG. 16B shows a center of percussion arm rotary system in accordance with at least one example of this disclosure.

FIG. 16B shows a center of percussion arm rotary system 1650 with a shorter arm 1652 where to get the mass and inertia balance needed to keep the center of percussion in the same position with respect to a square drive 1654, a distal end 1656 can have a hammerhead shape and a proximal end 1658 can be a simple beam shape. A tool 1660 can be held in a slot 1662 with a pin 1664 that fits in a hole 1666.

Any of the embodiments disclosed herein can enable advanced control where for a tool used and a state of the patient and the operation, the systems can automatically adjust the impact energy and frequency. To achieve intelligent control of the tools as an operation progresses, sensors such as sensors 524 can be used to monitor a position of the tool holding element with respect to a rotary electric surgical hammer impact tool or the position sensor included in tube motors may be used. In addition, an accelerometer in the tool (or its adaptor element that enables its proper positioning with respect to a tool holder element) also can provide additional feedback to enable ascertaining the progress of the tool into the bone. A camera can look upon the operation to also monitor progress of the tool into the bone with each impact, and information from the camera and the accelerometer can be sent to control electronics, such as control electronics 204, by a wired or a wireless link. From the position information from sensor, velocity and acceleration information can be obtained in order to allow for intelligent control of the amount of impact and its frequency to be delivered to a tool holder element.

Figure 17A:
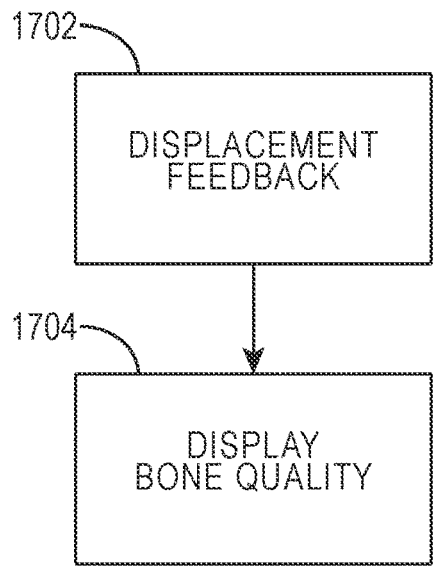
FIGS. 17A, 17B, and 17C show options for bone quality assessment consistent with at least one example of this disclosure.
Figure 17B:
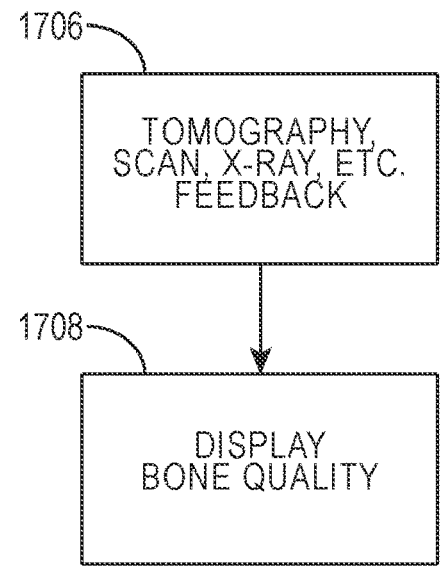
Figure 17C:
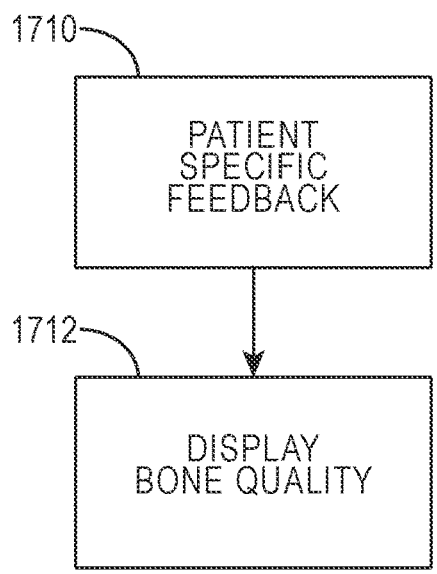

FIGS. 17A, 17B, and 17C show options for bone quality assessment consistent with at least one embodiment of this invention. Input into a controller of an initial assessment by a surgeon of the bone quality (e.g., the surgeon inputting the bone quality into a tool or some user interface, or some outside assessment of bone quality via X-ray or CT), which the surgeon can speak to the tool and a microphone, receives the words. Using a wireless link, the controller of the tool can access an external computer, which could process the information and a control plan can be downloaded to the tool and used to better control the tool for the operation at hand.

As shown in FIG. 17A, the various linear electric surgical hammer impact tools disclosed herein can provide feedback as to displacement of tools (1702). Based on the displacement, a bone quality can be determined. For example, large displacements can mean poor quality as the tool easily displaces bone. Small displacement may be higher bone quality since the tool is not able to displace as much bone for a given setting. Once an estimation of the bone quality is made, the value can be displayed to the surgeon (1704).

As shown in FIG. 17B, tomography scan, x-rays, or other scan data can be used to form an estimation of bone quality (1706). For example, if x-rays are faint, then bone density may be low and low bone density can be equated to poor bone quality. Dark and/or clear x-rays may indicate dense bone having a higher bone quality. Once an estimation of the bone quality is made, the value can be displayed to the surgeon (1708).

As shown in FIG. 17C, a surgeon can enter various factors for a patient, such as age, gender, race, data from pre-operative scans, etc. (1710). Using the various data, a computing system can use lookup tables, actuarial tables, anonymized data from other patients, etc. to formulate an estimate of bone quality. Based on the various factors, the estimated bone quality can be determined and displayed to the surgeon (1712).

Figure 18:
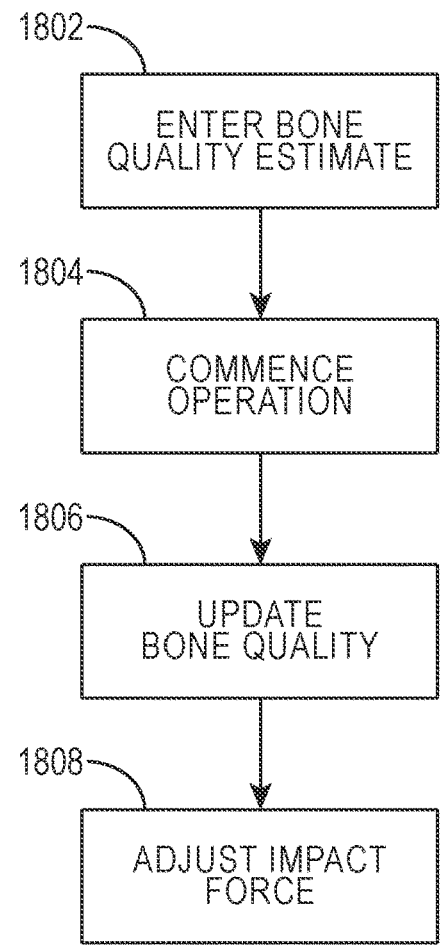
FIG. 18 shows a flowchart of logic usable for controlling a linear electric surgical hammer impact tool consistent with at least one example of this disclosure.

FIG. 18 shows a method for controlling a linear electric surgical hammer impact tool consistent with at least one example of this disclose. Once the bone quality is assessed and entered into a controller (1802), the operation may commence (1804). For example, bone quality scores can range from 1, poor quality bone, to 5 for high quality bone. Depending on the bone quality the tool may be set to deliver a predetermine impact force. For example, for low bone quality a low impact force can be set. For a higher bone quality, a higher impact force can be set.

During the operation, the bone quality can be updated (1806), using the tool/position sensor sensing, based on how quick the tool is moving into the bone on the first few broaches. For example, if the broach is sliding in faster than expected due to weak cancellous bone (e.g., osteoporosis), the bone quality can be updated. The goal of the initial bone quality assessment can be to modulate the starting force (initial impact) and adjust the amount of subsequent impact modulation as the tool progresses into the bone (1808). As the tool keeps impacting as broaches are increased in size, for example, the energy is monitored and remains unchanged when there is "maximum" broach movement down the femoral canal (as measured by the position sensor) for example.

Updating the bone quality can be a continuous process. For example, as the position sensor notes that the broach or implant is not advancing forward as much ("medium movement forward"), which can indicate the end of travel. Continuing to impact the bone harder may damage the bone so the tool can automatically modulate the force down a specific percentage (e.g., a more significant decrease for weaker bone, less significant for stronger bone, etc.).

Figure 19:
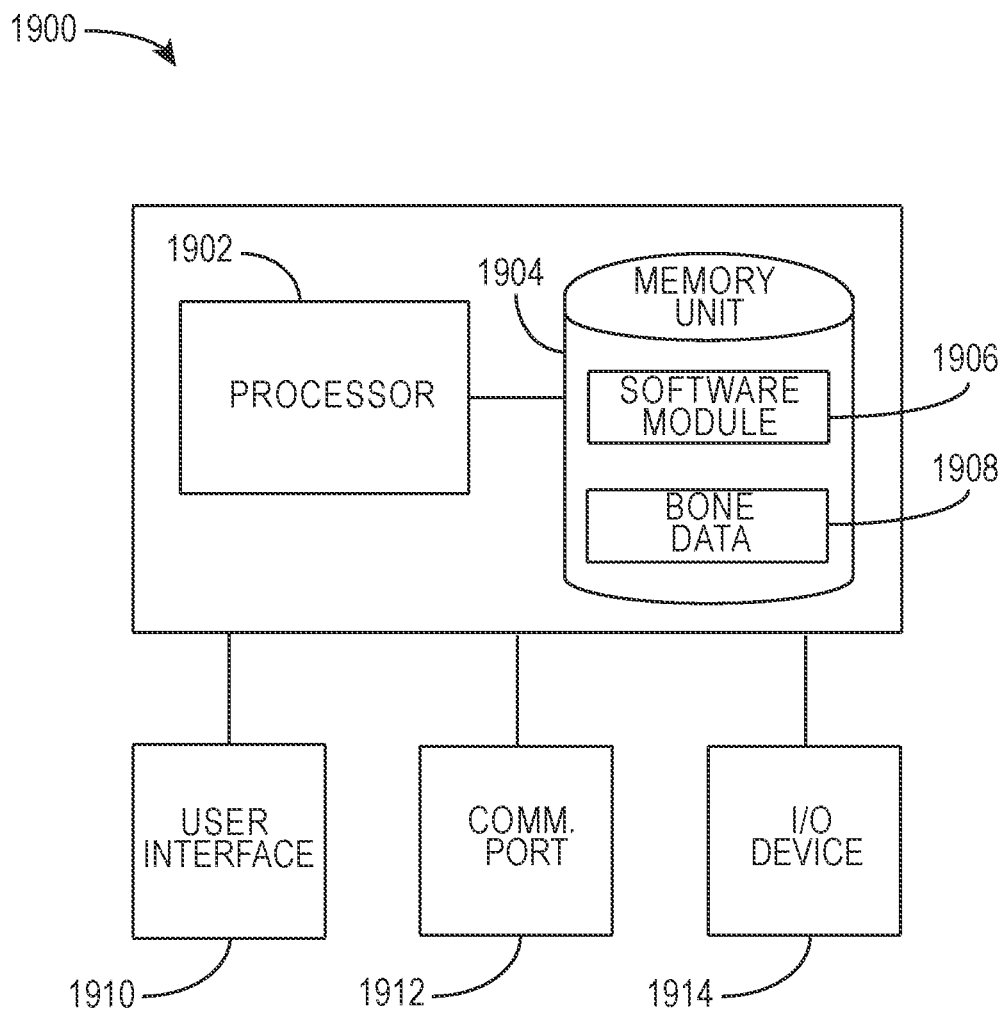
FIG. 19 shows a schematic of a controller consistent with at least one example of this disclosure.

FIG. 19 shows an example schematic of controller 1900, such as the electronics 204, in accordance with at least one example of this disclosure. As shown in FIG. 19, controller 1900 can include a processor 1902 and a memory 1904. The memory unit 1904 can include a software module 1906 and bone data 1908. While executing on the processor 1902, the software module 1906 can perform processes receiving displacement data, determining bone quality, adjusting an impact force of a tool, etc., including, for example, one or more stages included in the methods described with respect to FIGS. 17 and 18. As disclosed herein, bone data 1908 can include formulas, lookup tables, actuarial tables, patient data, etc. that can be used to determine bone quality as disclosed herein. Bone data 1908 can also include data for correlating impact forces desirable for given bone qualities and for various sizing of tools, such as rasps and/or broaches. Controller 1900 can also include a user interface 1910, a communications port 1912, and an input/output (I/O) device 1914.

The user interface 1910 can include any number of devices that allow a user to interface with the controller 1900. Non-limiting examples of the user interface 1910 can include a keypad, such as buttons located on a housing of a linear electric surgical hammer impact tool, a microphone, a display (touchscreen or otherwise and connected to the controller 1900 via a wired or wireless connection), etc.

The communications port 1912 may allow the controller 1900 to communicate with various information sources and devices, such as, but not limited to, remote computing devices such as servers or other remote computers. For example, remote computing devices may maintain data, such as patient scan data, that can be retrieved by the controller 1900 using the communications port 1912. Non-limiting examples of the communications port 1912 can include, Ethernet cards (wireless or wired), Bluetooth® transmitters and receivers, near-field communications modules, etc.

The I/O device 1914 can allow the controller 1900 to receive and output information. Non-limiting examples of the I/O device 1914 can include, sensors, such as Hall effect sensors, a camera (still or video), a microphone, etc. For example, the I/O device 1914 can allow the controller 1900 to directly receive patient data from a CT scanning device, x-ray machine, etc. As another example, the I/O device 1914 can include a Hall effect sensor that transmits one or more signals received by the processor 1902. The processor 1902 can then determine a position of a rotary element and/or an impact force to be generated by the slider based on the position of the slider.

Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A rotary electric surgical hammer impact tool comprising:
    a tool body;
    a motor located within the tool body;
    a shaft operatively coupled to the motor;
    a disk hammer element connected to the shaft, the disk hammer element including a radial impact projection; and
    a tool holder element comprising a shaft configured to support an implement at one end, the shaft of the tool holder element comprising a C-shaped structure straddling the disk hammer element and including opposing forward and rearward impact faces that are spaced,
    wherein the tool holder element is configured to move axially within the tool body when the implement is pressed against a work surface to bring the forward impact face into alignment to be engaged by the radial impact projection to impart forward impacts to the tool holder element, and
    wherein the tool holder element is configured to move axially within the tool body when the tool is pulled away from the work surface to bring the rearward impact face into alignment to be engaged by the radial impact projection to impart rearward impacts to the tool holder element.

2. The rotary electric surgical hammer impact tool of claim 1, wherein a rotational direction of the shaft connected to the motor is changed from a first direction for delivering forward impacts to a second direction for delivering rearward impacts.

3. The rotary electric surgical hammer impact tool of claim 1, further comprising bearings supporting the shaft of the tool holder element.

4. The rotary electric surgical hammer impact tool of a claim 1, wherein the motor is configured to rotate the disk hammer element over a partial revolution to deliver the impacts.

5. The rotary electric surgical hammer impact tool of claim 1, wherein the radial impact projection of the disk hammer element has a metallic impact surface.

6. The rotary electric surgical hammer impact tool of claim 1, wherein the radial impact projection of the disk hammer element has a polymer material impact surface.

7. The rotary electric surgical hammer impact tool of claim 1, further comprising:
    a sensor arranged to detect impacts on the toll holder element, and a controller configured to reverse rotation of motor to reverse rotation of the disk hammer element.

8. The rotary electric surgical hammer impact tool of claim 1, further comprising a control electronics and a battery in electrical communication with the control electronics, the control electronics and the battery disposed within the tool body.

9. The rotary electric surgical hammer impact tool of claim 1, wherein the shaft of the tool holder element is arranged generally perpendicular to a rotational axis of the motor.

10. The rotary electric surgical hammer impact tool of claim 1, further comprising a handle extending perpendicular to the tool body.

11. The rotary electric surgical hammer impact tool of claim 1, further comprising a microphone disposed in the tool body and in electrical communication with a controller, the controller configured to activate the motor based upon voice commands.

12. The rotary electric surgical hammer impact tool of claim 1, wherein the disk hammer element includes a plurality of swinging hammer elements mounted thereon.

13. The rotary electric surgical hammer impact tool of claim 1, further comprising a controller operative to perform operations comprising:
    determining an estimate of a bone quality; and
    increasing or decreasing an impact force generated by the linear electric surgical hammer impact tool based on the estimate of the bone quality.

14. The rotary electric surgical hammer impact tool of claim 1, further comprising a controller operative to perform operations comprising:
    determining a displacement of a tool attached to the tool holder; and
    increasing or decreasing an impact force generated by the linear electric surgical hammer impact tool based on the displacement of the tool.

15. A rotary electric surgical hammer impact tool comprising:
    an impact wrench having an impacting mechanism configured to deliver rotary impacts to an output shaft;
    an elongated tool arm mounted to the output shaft and extending perpendicular to an axis of the output shaft; and
    a tool implement mounted to an end of the elongated tool arm, the tool implement extending generally perpendicular to the end of the elongated tool arm.

16. The rotary electric surgical hammer impact tool of claim 15, wherein the tool implement is connected to the elongated tool arm by a pin.

17. A method of controlling a rotary electric surgical hammer impact tool for preparing a bone for receiving a prosthetic device, the method comprising:
    setting an initial impact force level of the rotary electric surgical hammer impact tool based upon an estimated bone quality;
    operating the rotary electric surgical hammer impact tool at the set initial impact level;
    monitoring an amount of a tool advancement into the bone; and
    increase or decreasing the impact level force by a predetermined amount based upon a detected amount of advancement of the tool into the bone.

18. The method of claim 17, further comprising monitoring an amount of a tool advancement into the bone and decreasing the impact level force by a predetermined amount based upon a detected amount of advancement of the tool into the bone.

19. The method of claim 17, wherein the bone quality is based upon a bone quality score including at least three bone quality levels.

20. The method according to claim 17, wherein the bone quality score is determined by detecting a position change of a broaching tool within a bone during an initial operation of the impact tool, wherein a maximum movement of the broaching tool indicates low bone quality, a mid-level of movement of the broaching tool means a medium bone quality and a minimal amount of movement of the broaching tool within the bone means a high bone quality.

* * * * *